(12) United States Patent
Mao et al.

(10) Patent No.: US 11,427,581 B2
(45) Date of Patent: Aug. 30, 2022

(54) JAK INHIBITOR AND USE THEREOF

(71) Applicant: ZHUHAI UNITED LABORATORIES CO., LTD., Guangdong (CN)

(72) Inventors: Weiwei Mao, Shanghai (CN); Hao Wu, Shanghai (CN); Xuejian Zheng, Shanghai (CN); Guoping Hu, Shanghai (CN); Changqing Wei, Shanghai (CN); Jian Li, Shanghai (CN); Shuhui Chen, Shanghai (CN)

(73) Assignee: ZHUHAI UNITED LABORATORIES CO., LTD., Guangdong (CN)

( * ) Notice: Subject to any disclaimer, the term of this patent is extended or adjusted under 35 U.S.C. 154(b) by 138 days.

(21) Appl. No.: 16/966,112

(22) PCT Filed: Jan. 31, 2019

(86) PCT No.: PCT/CN2019/074145
§ 371 (c)(1),
(2) Date: Jul. 30, 2020

(87) PCT Pub. No.: WO2019/149244
PCT Pub. Date: Aug. 8, 2019

(65) Prior Publication Data
US 2021/0070754 A1 Mar. 11, 2021

(30) Foreign Application Priority Data

Jan. 31, 2018 (CN) .......................... 201810096070.X
Aug. 23, 2018 (CN) .......................... 201810967605.6

(51) Int. Cl.
*C07D 471/04* (2006.01)
*A61P 19/02* (2006.01)
*C07D 513/04* (2006.01)

(52) U.S. Cl.
CPC ............ *C07D 471/04* (2013.01); *A61P 19/02* (2018.01); *C07D 513/04* (2013.01)

(58) Field of Classification Search
CPC .................................................. C07D 471/04
USPC ....................................................... 514/303
See application file for complete search history.

(56) References Cited

U.S. PATENT DOCUMENTS

2021/0171544 A1* 6/2021 Lee ...................... C07D 487/04

FOREIGN PATENT DOCUMENTS

CN 102105471 A 6/2011
CN 102459261 A 5/2012

OTHER PUBLICATIONS

C.J. Menet, et al. "Triazolopyridines as Selective JAK1 Inhibitors: From Hit Identification to GLPG0634", *J.Med.Chem*, vol. 57, Nov. 4, 2014 (Nov. 4, 2014), pp. 9323-9342.
Apr. 30, 2019 International Search Report issued in International Patent Application No. PCT/CN2019/074145.
Apr. 30, 2019 Written Opinion of the International Searching Authority issued in International Patent Application No. PCT/CN2019/074145.
Vainchenker W. et al.,JAKs in pathology: Role of Janus kinases in hematopoietic malignancies and immunodeficiencies, Seminars in Cell & Developmental Biology, 19(2008)385-393.
O'Shea J., et al., The Janus kinases (Jaks), Genome Biology, vol. 5—issue 12, article 253, 2004.
List Results for Search of JAK3; www.clinicaltrials.gov; retrieved Oct. 16, 2020; 8 pages.
Levy D., Loomis C., STAT3 Signaling and the Hyper-IgE Syndrome, The New England Journal of Medicine, vol. 357—issue 16, pp. 1655-1658, 2007.
Aug. 8, 2019 International Search Report issued in International Patent Application No. PCT/CN2019/074145.
Aug. 8, 2019 Written Opinion of the International Searching Authority issued in International Patent Application No. PCT/CN2019/074145.
Levy D., Loomis C., STAT3 Signaling and the Hyper-IgE Syndrome, The New England Journal of Medicine, vol. 357—issue 16, pp. 1655-1658, 2007.
Chinese Office Action regarding Patent Application No. 201980006488X, dated Mar. 17, 2022.

* cited by examiner

*Primary Examiner* — Kahsay Habte
(74) *Attorney, Agent, or Firm* — Harness, Dickey & Pierce, P.L.C.

(57) ABSTRACT

Disclosed in the present application are a class of compounds as JAK inhibitors and use thereof in the preparation of medicaments for treating JAK and TYK2 related diseases. Specifically, a compound represented by formula (I), an isomer thereof or a pharmaceutically acceptable salt thereof is disclosed.

12 Claims, 2 Drawing Sheets

JAK INHIBITOR AND USE THEREOF

CROSS-REFERENCE TO RELATED APPLICATIONS

This application is a U.S. National Phase Application under 35 U.S.C. 371 of International Application No. PCT/CN2019/074145, filed Jan. 31, 2019, which claims the benefit of Chinese Patent Application No. CN 201810096070.X, filed Jan. 31, 2018, and Chinese Patent Application No. CN 201810967605.6, filed Aug. 23, 2018. The entire disclosures of the above applications are incorporated herein by reference.

FIELD OF THE INVENTION

The present disclosure relates to a class of compounds as JAK inhibitors, and the use thereof in the manufacture of a medicament for the treatment of JAK and TYK2-related diseases. Specifically, disclosed is a compound of formula (I), an isomer thereof, or a pharmaceutically acceptable composition thereof.

Content of the Present Invention

JAK belongs to the tyrosine kinase family, which is involved in inflammation, autoimmune diseases, proliferative diseases, transplant rejection, diseases relating to damaged cartilage turnover, congenital cartilage malformations and/or diseases related to excessive IL6 secretion. The present disclosure also provides the compound, a method of producing a pharmaceutical composition containing the compound and a method of preventing and/or treating inflammation, autoimmune disease, proliferative disease, transplant rejection, diseases relating to damaged cartilage turnover, congenital cartilage malformation and/or diseases related to the excessive IL6 secretion by administering the compound of the present disclosure.

Janus kinase (JAK) is a cytoplasmic tyrosine kinase that transduces cytokine signals from membrane receptors to STAT transcription factors. The prior art has described four members of the JAK family which includes JAK1, JAK2, JAK3 and TYK2. When cytokines bind to their receptors, members of the JAK family self-phosphorylate and/or trans-phosphorylate with each other, then STATs phosphorylate, and then migrate into the nucleus to regulate transcription. JAK-STAT intracellular signal transduction is suitable for interferons, most interleukins, and a variety of cytokines and endocrine factors, such as EPO, TPO, GH, OSM, LIF, CNTF, GM-CSF and PRL (Vainchenker W. et al. (2008)).

The combined study of genetic models and small molecule JAK inhibitors revealed the therapeutic potential of several JAKs. It is confirmed by mouse and human genetics that JAK3 is a target for immunosuppression (O'Shea J. et al. (2004)). JAK3 inhibitors have been successfully used in clinical development, initially for organ transplant rejection, but later also for other immune inflammatory indications such as rheumatoid arthritis (RA), psoriasis and Crohn's disease (http://clinicaltrials.gov/). TYK2 is a potential target for immune inflammatory diseases, which has been confirmed by human genetics and mouse knockout studies (Levy D. and Loomis C. (2007)). JAK1 is a new target in the field of immuno-inflammatory diseases. Heterodimerize JAK1 with other JAKs to transduce cytokine-driven proinflammatory signaling. Therefore, inhibition of JAK1 and/or other JAK is expected to have therapeutic benefits for a range of inflammatory disorders and other diseases driven by JAK-mediated signal transduction.

Content of the Present Invention

The present disclosure provides a compound of formula (I), an isomer thereof or a pharmaceutically acceptable salt thereof,

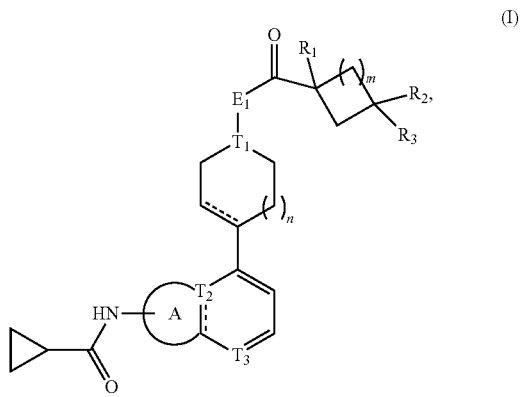

wherein,

⚹ is a single bond or a double bond;

m is 0 or 1;

n is 0 or 1;

$E_1$ is a single bond, —$CH_2$— or —NH—;

$T_1$ is CH or N;

$T_2$ is C or N;

$T_3$ is CH or N;

ring A is a 5-membered heteroaryl;

$R_1$ is H, F, Cl, Br, I, OH, $NH_2$, CN or a $C_{1-3}$ alkyl, wherein the $C_{1-3}$ alkyl is optionally substituted by one, two or three $R_a$;

each of $R_2$ and $R_3$ is independently H, F, Cl, Br, I, OH, $NH_2$ or CN;

$R_a$ is F, Cl, Br, I, OH or $NH_2$;

the 5-membered heteroaryl comprises 1, 2, 3 or 4 heteroatoms or heteroatom groups independently selected from the group consisting of —NH—, —O—, —S— and N.

In some embodiments of the present disclosure, $R_1$ is H, F, Cl, Br, I, OH, $NH_2$, CN or Me, and other variables are as defined in the present disclosure.

In some embodiments of the present disclosure, $R_2$ is H, F, Cl, Br, I, OH, $NH_2$ or CN, and other variables are as defined in the present disclosure.

In some embodiments of the present disclosure, $R_3$ is H, F, Cl, Br, I or OH, and other variables are as defined in the present disclosure.

In some embodiments of the present disclosure, ring A is 1,2,4-triazolyl or thiazolyl, and other variables are as defined in the present disclosure.

In some embodiments of the present disclosure, the structural unit

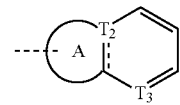

is

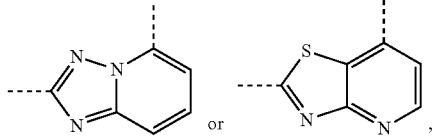

and other variables are as defined in the present disclosure.

In some embodiments of the present disclosure, the structural unit

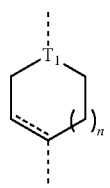

is

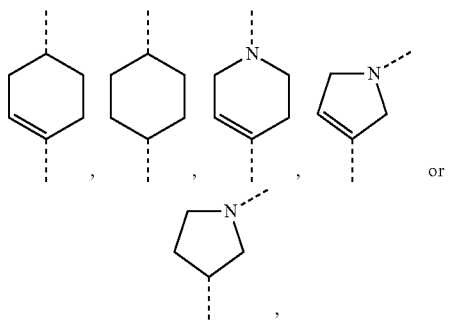

and other variables are as defined in the present disclosure.

Other embodiments of the present disclosure can be obtained by the arbitrary combination of variables mentioned above.

In some embodiments of the present disclosure, the compound, the isomer or the pharmaceutically acceptable salt thereof, the compound of which is selected from the group consisting of

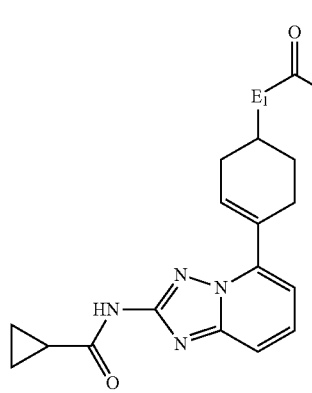
(I-1)

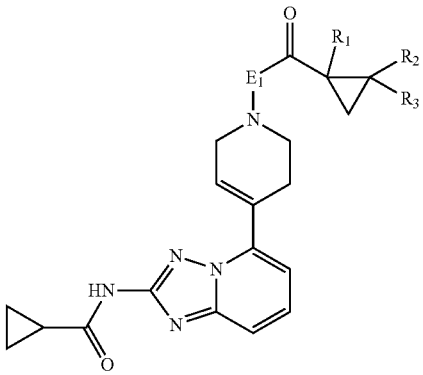
(I-2)

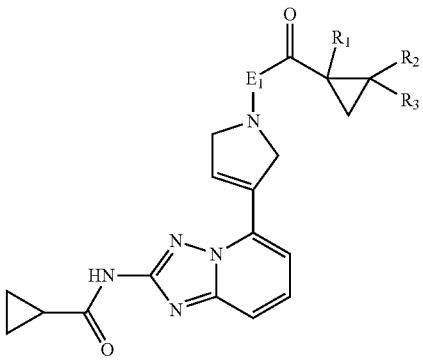
(I-3)

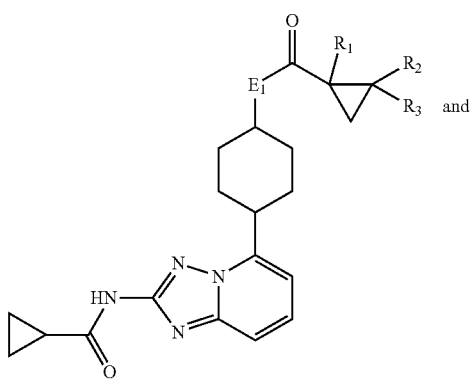
(I-4) and

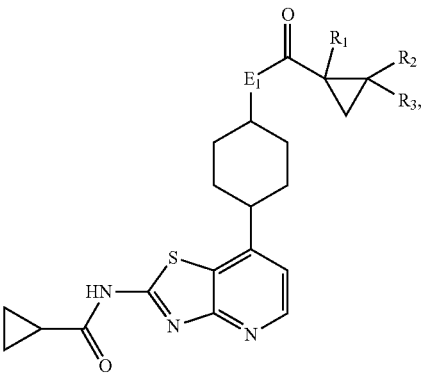
(I-5)

wherein, $E_1$, $R_1$, $R_2$ and $R_3$ are as defined in the present disclosure.

The present disclosure also provides a compound, an isomer or a pharmaceutically acceptable salt thereof, which is selected from the group consisting of

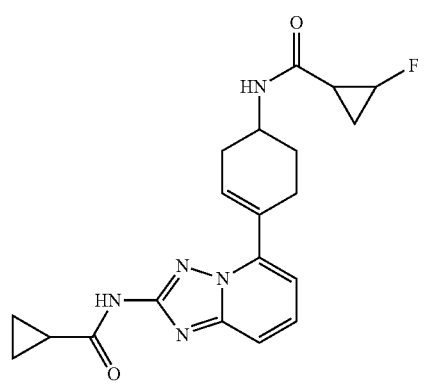
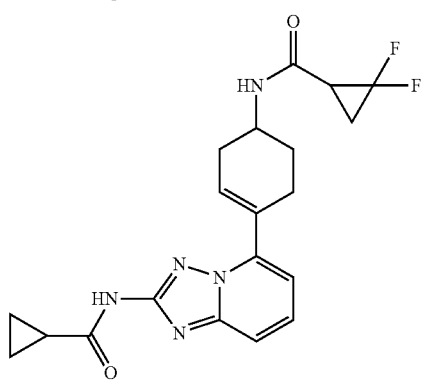
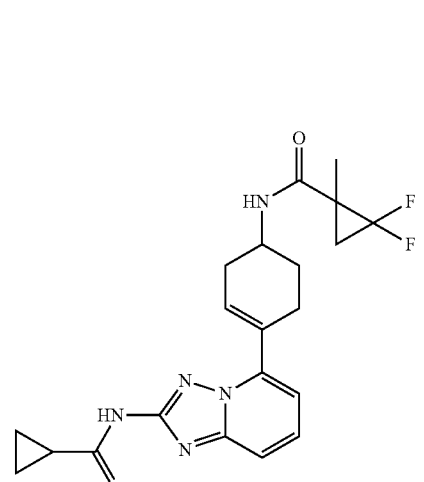
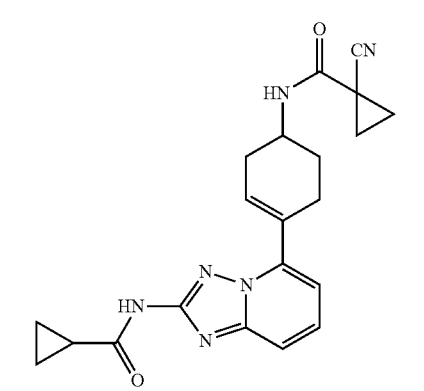
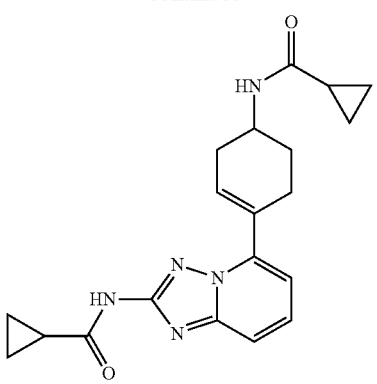
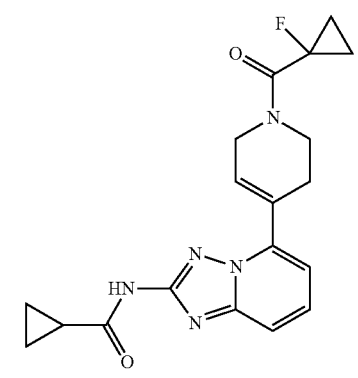
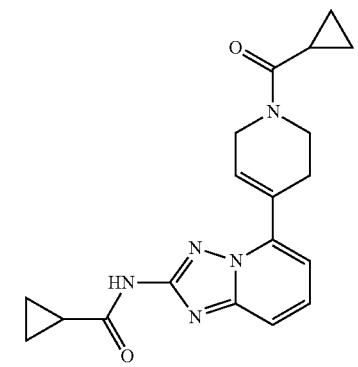
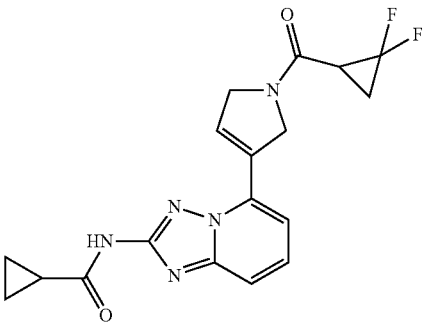

-continued
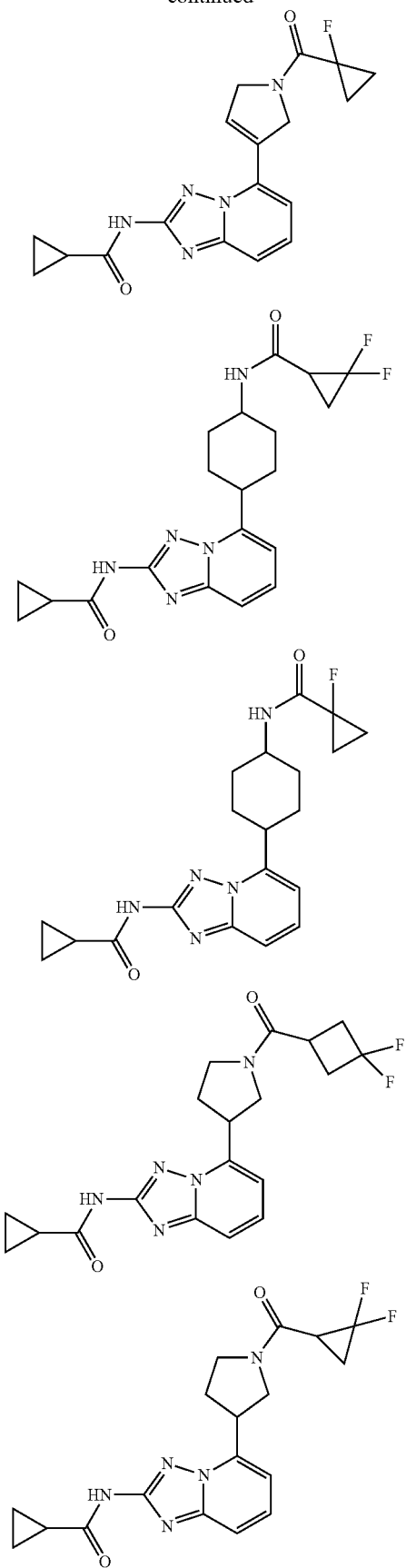
-continued
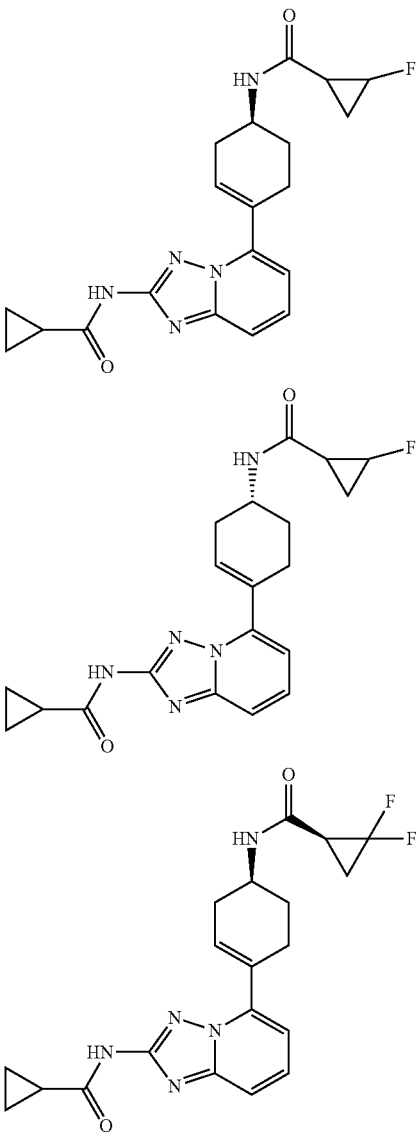
In some embodiments of the present disclosure, the compound, the isomer or the pharmaceutically acceptable salt thereof is selected from the group consisting of -continued
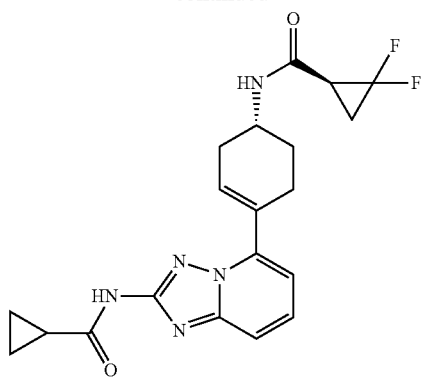
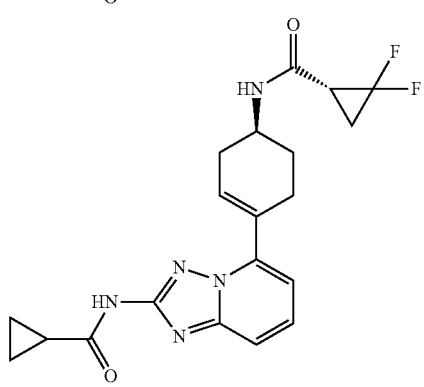
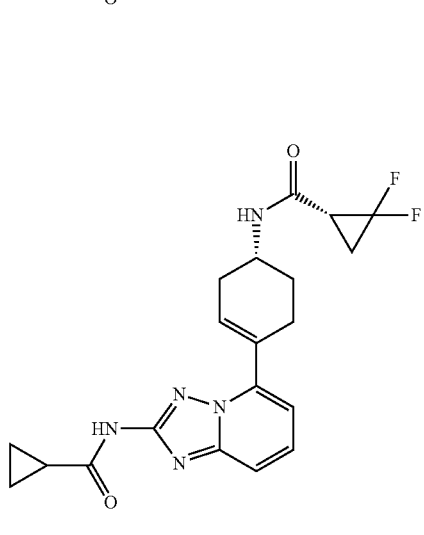
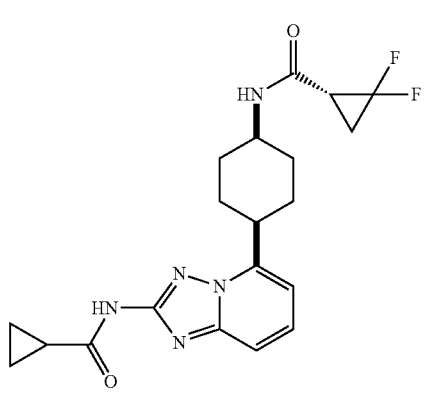
-continued
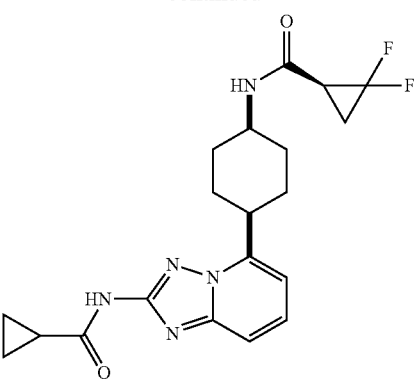
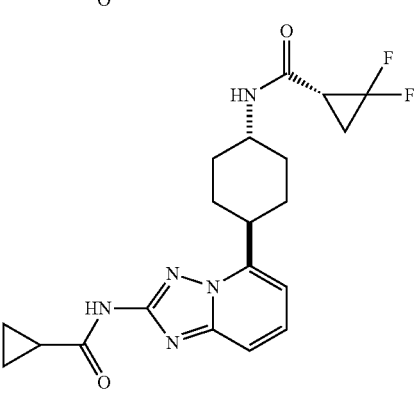
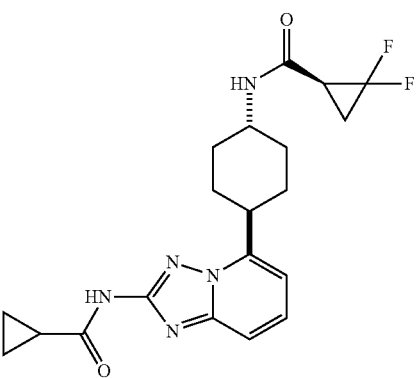
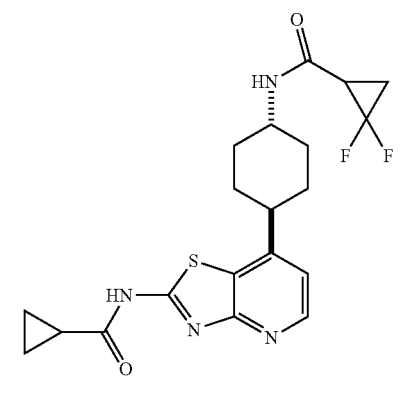

and

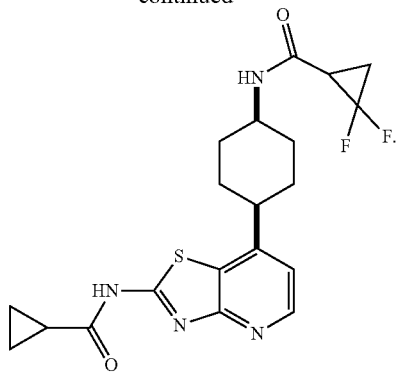

The disclosure also provides a pharmaceutical composition, which comprises a therapeutically effective amount of the compound, the isomer or the pharmaceutically acceptable salt thereof as an active ingredient, and a pharmaceutically acceptable carrier.

The present disclosure also provides a use of the compound or the pharmaceutically acceptable salt thereof or the pharmaceutical composition in the manufacture of a medicament for the treatment of JAK1 and TYK2 related diseases.

In some embodiments of the present disclosure, with respect to the use mentioned above, it is a medicament for the treatment of rheumatoid arthritis.

Technical Effects

The compounds of the present disclosure exhibit good selective inhibitory effects on the subtypes of TYK2 and JAK1 among all 4 subtypes of JAK kinase (JAK1, JAK2, JAk3 and TYK2) during the in vitro activity experiment, and these compounds exhibit a high exposure amount, good oral bioavailability in the pharmacokinetic experiments conducted on rats, which is beneficial for producing excellent in vivo effect.

Definition and Description

Unless otherwise indicated, the following terms when used in the descriptions and the claims of the present disclosure have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" used herein in terms of those compounds, materials, compositions, and/or dosage forms, are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid and methanesulfonic acid, and the like; and an salt of amino acid (such as arginine and the like), and a salt of an organic acid such as glucuronic acid and the like. Certain specific compounds of the present disclosure that contain both basic and acidic functional groups can be converted to any base or acid addition salt.

The pharmaceutically acceptable salt of the present disclosure can be prepared from the parent compound that contains an acidic or basic moiety by the conventional chemical method. Generally, such salt can be prepared by reacting the free acid or base form of the compound with a stoichiometric amount of an appropriate base or acid in water or an organic solvent or a mixture thereof.

In addition to the salt form, the compound provided by the present disclosure also exists in prodrug form. The prodrug of the compound described herein is the compound that readily undergoes chemical change under physiological condition to be converted into the compound of the present disclosure. Additionally, the prodrug can be converted to the compound of the present disclosure by a chemical or biochemical method in vivo environment.

Certain compounds of the present disclosure can exist in a non-solvated form or a solvated form, including hydrated form. Generally, the solvated form is equivalent to the non-solvated form, and both are encompassed within the scope of the present disclosure.

The compound of the present disclosure may have a specific geometric or stereoisomeric form. The present disclosure contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present disclosure. The substituent such as alkyl may have an additional asymmetric carbon atom. All these isomers and mixtures thereof are encompassed within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by a double bond or a single bond of a carbon atom on the ring which is incapable of free rotation.

Unless otherwise specified, the term "diastereomer" refers to stereoisomers in which the molecules have two or more chiral centers and are not mirror images of each other.

Unless otherwise specified, "(D)" or "(+)" stands for dextrorotation, "(L)" or "(−)" stands for levorotation, "(DL)" or "(±)" stands for racemization.

Unless otherwise specified, the absolute configuration of a stereogenic center is represented by a wedged solid bond (⬤) and a wedged dashed bond (⬤), and the relative configuration of a stereogenic center is represented by a straight solid bond (⬤) and a straight dashed bond (⬤). A wave line (⬤) represents a wedged solid bond (⬤) or a wedged dashed bond (⬤), or represents a straight solid bond (⬤) or a straight dashed bond (⬤).

The compounds of the present disclosure may be present in particular. Unless otherwise indicated, the terms "tautomer" or "tautomeric form" refer to the fact that the different functional isomers are in dynamic equilibrium at room temperature and can be rapidly converted into each other. If tautomers are possible (such as in solution), the chemical equilibrium of the tautomers can be achieved. For example, proton tautomers (also known as prototropic tautomers) include interconversions by proton transfer, such as keto-enol isomerization and imine-enamine isomerization. The valence tautomer includes the mutual transformation of the rearrangement of some bonding electrons. A specific example of keto-enol tautomerization is the interconversion between two tautomers of pentane-2,4-dione and 4-hydroxypent-3-en-2-one.

Unless otherwise specified, the terms "enriched in one isomer", "isomer enriched", "enriched in one enantiomer" or "enantiomer enriched" refer to the content of one of the isomers or enantiomers is less than 100% while is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise specified, the terms "excess of isomer" or "excess of enantiomer" refer to the difference between the relative percentages of the two isomers or enantiomers. For example, the content of one of the isomers or enantiomers is 90%, and the other one is 10%, then the excess of isomer or enantiomer (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivation of chiral auxiliary followed by separating the resulting diastereomeric mixture and cleaving the group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from an amine). The compound of the present disclosure may contain an unnatural proportion of atomic isotope at one or more than one atom(s) that constitutes the compound. For example, the compound can be radiolabeled with a radioactive isotope, such as tritium ($^3$H), iodine-125 ($^{125}$I) or C-14 ($^{14}$C). For another example, hydrogen can be replaced with heavy hydrogen to form a deuterated drug, and the bond composed of deuterium and carbon is stronger than that of common hydrogen and carbon. Compared with undeuterated drugs, deuterated drugs have advantages including reduced side effects and increased drug stability, enhanced the efficacy and prolonged biological half-life etc. All isotopic variations of the compound of the present disclosure, whether radioactive or not, are encompassed within the scope of the present disclosure.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom is replaced with substituent(s), including deuterium and hydrogen variants, as long as the valence of the specific atom is normal and the substituted compound is stable. When the substituent is an oxygen (i.e. =O), it means two hydrogen atoms are substituted. The substituent on an aromatic ring cannot be an oxo group. The term "optionally substituted" means an atom can be substituted with a substituent or not, unless otherwise specified. The type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two Rs, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one variable is absent, it means that the variable does not exist. For example, when X in A-X is absent, the structure of which is actually A. When a substituent listed is not indicated by which atom it connects to the group substituted, the substituent can bond to the group through any atom it contained, for example, pyridine as a substituent can connect to the group substituted through any carbon atoms on the pyridine.

When the enumerative linking group does not indicate the direction for linking, the direction for linking is arbitrary, for example, the linking group L contained in

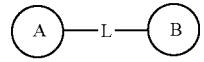

is -M-W—, then -M-W— can link ring A and ring B to form

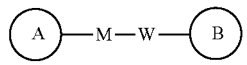

in the direction same as left-to-right reading order, and form

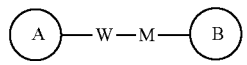

in the direction contrary to left-to-right reading order. Combinations of the linking groups, substituents and/or variants thereof are permissible only if such combinations result in stable compounds.

Unless otherwise specified, the term "hetero" represents a heteroatom or a heteroatomic group (e.g., a group containing a heteroatom), including the atoms except for carbon (C) and hydrogen (H) and the atomic groups containing these atoms, for example, including oxygen (O), nitrogen (N), sulfur (S), silicon (Si), germanium (Ge), aluminum (Al), boron (B), —O—, —S—, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O)N(H)—.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so called ring includes a single ring, as well as a double ring system or a multiple ring system such as a spiral ring, a fused ring or a bridged ring. The number of the atoms on the ring is usually defined as the member of the ring, for example, a "5-7-membered ring" means that 5 to 7 atoms are arranged on a ring. Unless otherwise specified, the ring optionally contains 1 to 3 heteroatoms. Therefore, a "5-7-membered ring" includes, for example, phenyl, pyridinyl and piperidinyl; on the other hand, the term "5-7-membered heterocycloalkyl" includes pyridyl and piperidinyl, but excluding phenyl. The term "ring" also includes a ring system containing at least one ring, wherein each ring independently meets the above definition.

Unless otherwise specified, the term "alkyl" refers to a linear chain or branched chain saturated hydrocarbon group. In some embodiments, the alkyl is a $C_{1-12}$ alkyl; in some other embodiments, the alkyl is a $C_{1-6}$ alkyl; in some other embodiments, the alkyl is a $C_{1-3}$ alkyl. It can be mono-substituted (e.g., —CH$_2$F) or multi-substituted (e.g., —CF$_3$), can be monovalent (e.g. methyl), divalent (e.g., methylene) or multivalent (e.g., methenyl). Examples of alkyl include but not limited to methyl (Me), ethyl (Et), propyl (including n-propyl and isopropyl), butyl (including n-butyl, isobutyl, s-butyl, t-butyl), pentyl (including n-pentyl, isopentyl, neopentyl) and hexyl and the like.

Unless otherwise specified, the term "alkenyl" refers to a linear chain or branched chain hydrocarbon group having one or more than one carbon-carbon double bond(s) at any position of the group. In some embodiments, the alkenyl is a $C_{2-8}$ alkenyl; in some other embodiments, the alkenyl is a $C_{2-6}$ alkenyl; in some other embodiments, the alkenyl is a $C_{2-4}$ alkenyl. It can be mono-substituted or multi-substituted, and can be monovalent, divalent or multivalent. Examples of the alkenyl include but not limited to ethenyl, propenyl, butenyl, pentenyl, hexenyl, butadienyl, pentadienyl, hexadienyl, and the like.

Unless otherwise specified, the term "alkynyl" refers to a linear chain or branched chain hydrocarbon group having one or more than one carbon-carbon triple bond(s) at any position of the group. In some embodiments, the alkynyl is a $C_{2-8}$ alkynyl; in some other embodiments, the alkynyl is a $C_{2-6}$ alkynyl; in some other embodiments, the alkynyl is a $C_{2-4}$ alkynyl. It can be mono-substituted or multi-substituted, and can be monovalent, divalent or multivalent. Examples of the alkynyl include but not limited to ethynyl, propynyl, butynyl, pentynyl, and the like.

Unless otherwise specified, the term "heteroalkyl", by itself or in combination with another term, refers to a stable linear or branched chain alkyl or a combination thereof having a specified number of carbon atoms and at least one heteroatom or heteroatomic group. In some embodiments, the heteroatom is B, O, N or S, wherein the nitrogen and sulfur atoms are optionally oxidized and the nitrogen atom is optionally quaternized. In some other embodiments, the heteroatomic group is —C(=O)O—, —C(=O)—, —C(=S)—, —S(=O), —S(=O)$_2$—, —C(=O)N(H)—, —N(H)—, —C(=NH)—, —S(=O)$_2$N(H)— or —S(=O)N(H)—. In some embodiments, the heteroalkyl is a $C_{1-6}$ heteroalkyl; in some other embodiments, the heteroalkyl is a $C_{1-3}$ heteroalkyl. The heteroatom or heteroatomic group can be located at any interior position of the heteroalkyl, including the position where the alkyl attaches to the rest of the molecule. But the terms "alkoxy", "alkylamino" and "alkylthio" (or thioalkoxy) are used in their conventional meanings and refer to an alkyl group connected to the rest of the molecule via an oxygen atom, an amino or a sulfur atom respectively. Examples of the heteroalkyl include, but not limited to, —OCH$_3$, —OCH$_2$CH$_3$, —OCH$_2$CH$_2$CH$_3$, —OCH$_2$(CH$_3$)$_2$, —CH$_2$—CH$_2$—O—CH$_3$, —NHCH$_3$, —N(CH$_3$)$_2$, —NHCH$_2$CH$_3$, —N(CH$_3$)(CH$_2$CH$_3$), —CH$_2$—CH$_2$—NH—CH$_3$, —CH$_2$—CH$_2$—N(CH$_3$)—CH$_3$, —SCH$_3$, —SCH$_2$CH$_3$, —SCH$_2$CH$_2$CH$_3$, —SCH$_2$(CH$_3$)$_2$, —CH$_2$—S—CH$_2$—CH$_3$, —CH$_2$—CH$_2$, —S(=O)—CH$_3$, —CH$_2$—CH$_2$—S(=O)$_2$—CH$_3$, —CH=CHO—CH$_3$, —CH$_2$—CH=N—OCH$_3$ and —CH=CH—N(CH$_3$)—CH$_3$. Up to two consecutive heteroatoms can be present, such as, —CH$_2$—NH—OCH$_3$.

Unless otherwise specified, the term "heteroalkenyl", by itself or in combination with another term, refers to a stable linear or branched chain alkenyl or a combination thereof having a specified number of carbon atoms and at least one heteroatom or heteroatomic group. In some embodiments, the heteroatom is B, O, N or S, wherein the nitrogen and sulfur atoms are optionally oxidized and the nitrogen atom is optionally quaternized. In some other embodiments, the heteroatomic group is —C(=O)O—, —C(=O)—, —C(=S)—, —S(=O), —S(=O)$_2$—, —C(=O)N(H)—, —N(H)—, —C(=NH)—, —S(=O)$_2$N(H)— or —S(=O)N(H)—. In some embodiments, the heteroalkenyl is a $C_{2-6}$ heteroalkenyl; in some other embodiments, the heteroalkyl is a $C_{2-4}$ heteroalkenyl. The heteroatom or heteroatomic group can be located at any interior position of the heteroalkenyl, including the position where the alkenyl attaches to the rest of the molecule. But the terms "alkenyloxy", "alkenylamino" and "alkenylthio" are used in their conventional meanings and refer to an alkenyl group connected to the rest of the molecule via an oxygen atom, an amino or a sulfur atom respectively. Examples of the heteroalkenyl include, but not limited to, —O—CH=CH$_2$, —O—CH=CHCH$_3$, —O—CH=C(CH$_3$)$_2$, —CH=CH—O—CH$_3$, —O—CH=CHCH$_2$CH$_3$, —CH$_2$—CH=CH—OCH$_3$, —NH—CH=CH$_2$, —N(CH=CH$_2$)—CH$_3$, —CH=CH—NH—CH$_3$, —CH=CH—N(CH$_3$)$_2$, —S—CH=CH$_2$, —S—CH=CHCH$_3$, —S—CH=C(CH$_3$)$_2$, —CH$_2$—S—CH=CH$_2$, —S(=O)—CH=CH$_2$ and —CH=CH—S(=O)$_2$—CH$_3$. Up to two consecutive heteroatoms can be present, such as, —CH=CH—NH—OCH$_3$.

Unless otherwise specified, the term "heteroalkynyl", by itself or in combination with another term, refers to a stable linear or branched chain alkynyl or a combination thereof having a specified number of carbon atoms and at least one heteroatom or heteroatomic group. In some embodiments, the heteroatom is B, O, N or S, wherein the nitrogen and sulfur atoms are optionally oxidized and the nitrogen atom is optionally quaternized. In some other embodiments, the heteroatomic group is —C(=O)O—, —C(=O)—, —C(=S)—, —S(=O), —S(=O)$_2$—, —C(=O)N(H)—, —N(H)—, —C(=NH)—, —S(=O)$_2$N(H)— or —S(=O)N(H)—. In some embodiments, the heteroalkynyl is a $C_{2-6}$ heteroalkynyl; in some other embodiments, the heteroalkyl is a $C_{2-4}$ heteroalkynyl. The heteroatom or heteroatomic group can be located at any interior position of the heteroalkynyl, including the position where the alkynyl attaches to the rest of the molecule. But the terms "alkynyloxy", "alkynylamino" and "alkynylthio" are used in their conventional meanings and refer to an alkynyl group connected to the rest of the molecule via an oxygen atom, an amino or a sulfur atom respectively. Examples of the heteroalkynyl include, but not limited to,

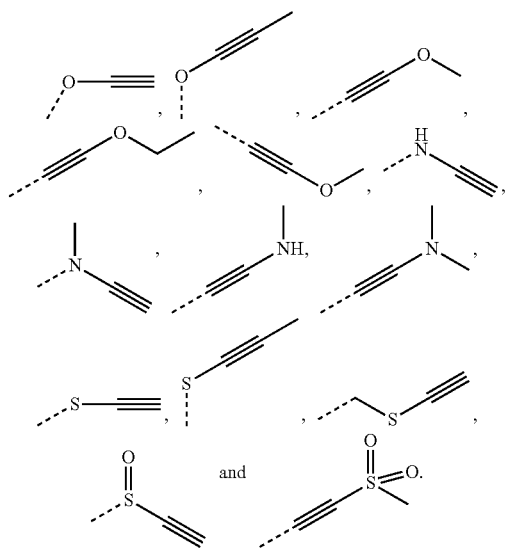

consecutive heteroatoms can be present, such as

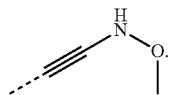

Unless otherwise specified, "cycloalkyl" includes any stable cyclic alkyl including monocyclic, bicyclic, or tricyclic systems, wherein the bicyclic and tricyclic systems include spiro, fused, and bridged rings. In some embodiments, the cycloalkyl is a $C_{3-8}$ cycloalkyl; in some other embodiments, the cycloalkyl is a $C_{3-4}$ cycloalkyl; in some other embodiments, the cycloalkyl is a $C_{5-6}$ cycloalkyl. It can be mono-substituted or multi-substituted, and can be monovalent, divalent or multivalent. Examples of the cycloalkyl include, but not limited to, cyclopropyl, cyclobutyl, cyclopentyl, cyclohexyl, cycloheptyl, norbornanyl, [2.2.2]bicyclooctane, [4.4.0]bicyclodecane and the like.

Unless otherwise specified, "cycloalkenyl" includes any stable cyclic alkenyl having one or more than one unsaturated carbon-carbon double bond(s) at any position of the group, including monocyclic, bicyclic, or tricyclic systems, wherein the bicyclic and tricyclic systems include spiro, fused, and bridged rings, but any ring in these systems is non-aromatic. In some embodiments, the cycloalkenyl is a $C_{3-8}$ cycloalkenyl; in some other embodiments, the cycloalkenyl is a $C_{3-6}$ cycloalkenyl; in some other embodiments, the cycloalkenyl is a $C_{5-6}$ cycloalkenyl. It can be mono-substituted or multi-substituted, and can be monovalent, divalent or multivalent. Examples of the cycloalkenyl include, but not limited to, cyclopentenyl, cyclohexenyl and the like.

Unless otherwise specified, "cycloalkynyl" includes any stable cyclic alkynyl having one or more than one carbon-carbon triple bonds at any position of the group, including monocyclic, bicyclic, or tricyclic systems, wherein the bicyclic and tricyclic systems include spiro, fused, and bridged rings. It can be mono-substituted or multi-substituted, and can be monovalent, divalent or multivalent.

Unless otherwise specified, the term "heterocycloalkyl", by itself or in combination with another term, refers to a cyclized "heteroalkyl", including monocyclic, bicyclic, or tricyclic systems, wherein the bicyclic and tricyclic systems include spiro, fused, and bridged rings. In addition, in terms of the "heterocycloalkyl", the heteroatom can occupy the position through which the heterocycloalkyl is attached to the rest of the molecule. In some embodiments, the heterocycloalkyl is a 4-6 membered heterocycloalkyl; in some other embodiments, the heterocycloalkyl is a 5-6 membered heterocycloalkyl. Examples of the heterocycloalkyl include, but not limited to, azetidinyl, oxetanyl, thiacyclobutanyl, pyrrolidinyl, pyrazolidinyl, imidazolidinyl, tetrahydrothiophenyl (including tetrahydrothiophen-2-yl and tetrahydrothiophen-3-yl etc.), tetrahydrofuranyl (including tetrahydrofuran-2-yl etc.), tetrahydropyranyl, piperidinyl (including 1-piperidinyl, 2-piperidinyl and 3-piperidinyl etc.), piperazinyl (including 1-piperazinyl and 2-piperazinyl etc.), morpholinyl (including 3-morpholinyl and 4-morpholinyl etc.), dioxanyl, dithianyl, isoxazolidinyl, isothiazolidinyl, 1,2-oxazinyl, 1,2-thiazinyl, hexahydropyridazinyl, homopiperazinyl, homopiperidinyl or oxepanyl.

Unless otherwise specified, the term "heterocycloalkenyl", by itself or in combination with another term, refers to a cyclized "heteroalkenyl", including monocyclic, bicyclic, or tricyclic systems, wherein the bicyclic and tricyclic systems include spiro, fused, and bridged rings, but any ring in these systems is non-aromatic. In addition, in terms of the "heterocycloalkenyl", the heteroatom can occupy the position through which the heterocycloalkenyl is attached to the rest of the molecule. In some embodiments, the heterocycloalkenyl is a 4-6 membered heterocycloalkenyl; in other embodiments, the heterocycloalkenyl is a 5-6 membered heterocycloalkenyl. Examples of the heterocycloalkenyl include, but not limited to,

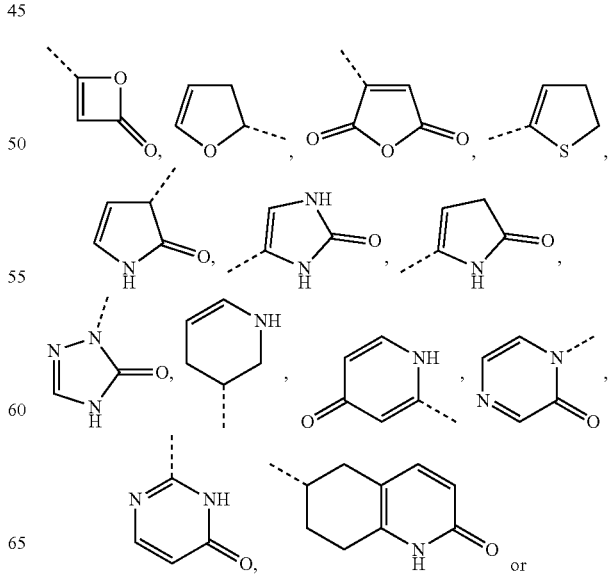

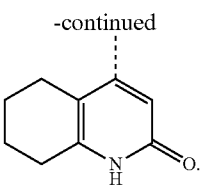

Unless otherwise specified, the term "heterocycloalkynyl", by itself or in combination with another term, refers to a cyclized "heteroalkynyl", including monocyclic, bicyclic, or tricyclic systems, wherein the bicyclic and tricyclic systems include spiro, fused, and bridged rings. In addition, in terms of the "heterocycloalkynyl", a heteroatom can occupy the position through which the heterocycloalkynyl is attached to the rest of the molecule. In some embodiments, the heterocycloalkynyl is a 4-6 membered heterocycloalkynyl; in some other embodiments, the heterocycloalkynyl is a 5-6 membered heterocycloalkynyl. Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like. Unless otherwise specified, examples of the haloalkyl include, but not limited to trifluoromethyl, trichloromethyl, pentafluoroethyl and pentachloroethyl.

The term "alkoxy" refers to an alkyl as defined above having a specified number of carbon atoms linking by an oxygen bridge. Unless otherwise specified, $C_{1-6}$ alkoxy includes $C_1$, $C_2$, $C_3$, $C_4$, $C_5$ and $C_6$ alkoxy. In some embodiments, the alkoxy is a $C_{1-3}$ alkoxy. Examples of the alkoxy include, but not limited to methoxy, ethoxy, n-propoxy, isopropoxy, n-butoxy, sec-butoxy, tert-butoxy, n-pentyloxy and S-pentoxy.

Unless otherwise specified, the terms "aromatic ring" and "aryl" in the present disclosure can be used interchangeably. The term "aromatic ring" or "aryl" refers to a polyunsaturated carbocyclic system, which can be monocyclic, bicyclic or polycyclic systems, in which at least one ring is aromatic, and the rings in the bicyclic and polycyclic systems are fused together. It can also be mono- or poly-substituted, and can be monovalent, divalent or polyvalent. In some embodiments, the aryl is a $C_{6-12}$ aryl; in some other embodiments, the aryl is a $C_{6-10}$ aryl. Examples of the aryl include, but not limited to, phenyl, naphthyl (including 1-naphthyl, 2-naphthyl, etc.). The substituent of any one of the above aryl ring systems is the acceptable substituents described in the present disclosure.

Unless otherwise specified, the terms "heteroaromatic ring" and "heteroaryl" in the disclosure can be used interchangeably. The term "heteroaryl" refers to an aryl (or an aromatic ring) containing 1, 2, 3 or 4 heteroatoms independently selected from the group consisting of B, N, O and S, which can be monocyclic, bicyclic, or tricyclic systems, wherein the nitrogen atom can be substituted or unsubstituted (i.e., N or NR, wherein R is H or the substituent as defined herein), and optionally quaternized and the nitrogen and sulfur heteroatoms can optionally be oxidized (i.e., NO and $S(O)_p$, p is 1 or 2). The heteroaryl can be connected to the rest of the molecule via a heteroatom. In some embodiments, the heteroaryl is a 5-10 membered heteroaryl; in some other embodiments, the heteroaryl is a 5-6 membered heteroaryl. Examples of the heteroaryl include, but not limited to, pyrrolyl (including N-pyrrolyl, 2-pyrrolyl and 3-pyrrolyl, etc.), pyrazolyl (including 2-pyrazolyl and 3-pyrazolyl, etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazolyl and 5-thiazolyl, etc.), furanyl (including 2-furanyl and 3-furanyl, etc.), thiophenyl (including 2-thiophenyl and 3-thiophenyl, etc.), pyridyl (including 2-pyridyl, 3-pyridyl and 4-pyridyl, etc.), pyrazinyl, pyrimidinyl (including 2-pyrimidinyl and 4-pyrimidinyl, etc.), benzothiazolyl (including 5-benzothiazolyl, etc.), purinyl, benzimidazolyl (including 2-benzimidazolyl, etc.), indolyl (including 5-indolyl, etc.), isoquinolinyl (including 1-isoquinolinyl and 5-isoquinolinyl, etc.), quinoxalinyl (including 2-quinoxalinyl and 5-quinoxalinyl, etc.), quinolinyl (including 3-quinolinyl and 6-quinolinyl, etc.), pyrazinyl, purinyl, benzoxazolyl. The substituent of any heteroaryl ring system is the acceptable substituents of the present disclosure.

Unless otherwise specified, the term "aralkyl" is intended to include those groups in which an aryl is attached to an alkyl. In some embodiments, the aralkyl is $C_{6-10}$ aryl-$C_{1-4}$ alkyl; in some other embodiments, the aralkyl is $C_{6-10}$ aryl-$C_{1-2}$ alkyl. Examples of the aralkyl include, but not limited to, benzyl, phenethyl, naphthylmethyl, and the like. "Aryloxy" and "arylthio" represent those groups in which a carbon atom (such as methyl) in the aralkyl group is replaced with an oxygen atom and a sulfur atom, respectively. In some embodiments, the aryloxy is $C_{6-10}$ aryl-O—$C_{1-2}$ alkyl; in some other embodiments, the aryloxy is $C_{6-10}$ aryl-$C_{1-2}$ alkyl-O—. In some embodiments, the arylthio is $C_{6-10}$ aryl-S—$C_{1-2}$ alkyl; in some other embodiments, the arylthio is $C_{6-10}$ aryl-$C_{1-2}$ alkyl-S—. Examples of the aryloxy and the arylthio include, but not limited to, phenoxymethyl, 3-(1-naphthyloxy)propyl, phenylthiomethyl, and the like.

Unless otherwise specified, the term "heteroaralkyl" is intended to include those groups in which a heteroaryl is attached to an alkyl. In some embodiments, the heteroaralkyl is 5-8 membered heteroaryl-$C_{1-4}$ alkyl; in some other embodiments, the heteroaralkyl is 5-6 membered heteroaryl-$C_{1-2}$ alkyl. Examples of the heteroaralkyl include, but are not limited to, pyrrolylmethyl, pyrazolylmethyl, pyridylmethyl, pyrimidinylmethyl, and the like. "Heteroaryloxy" and "heteroarylthio" refer to those groups in which a carbon atom (such as methyl) in the heteroaralkyl is replaced with an oxygen atom and a sulfur atom, respectively. In some embodiments, the heteroaryloxy is 5-8 membered heteroaryl-O—$C_{1-2}$ alkyl; in some other embodiments, the heteroaryloxy is 5-6 membered heteroaryl-$C_{1-2}$ alkyl-O—. In some embodiments, the heteroarylthio group is 5-8 membered heteroaryl-S—$C_{1-2}$ alkyl; in some other embodiments, the heteroarylthio group is 5-6 membered heteroaryl-$C_{1-2}$ alkyl-S—. Examples of the heteroaryloxy and the heteroarylthio include, but not limited to, pyrrolyloxymethyl, pyrazolyloxymethyl, 2-pyridyloxymethyl, pyrrolylthiomethyl, pyrazolylthiomethyl, 2-pyridylthiomethyl, and the like.

Unless otherwise specified, $C_{n-n+m}$ or $C_n$—$C_{n+m}$ includes any one of the specific cases of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$, and also includes any one of the ranges between n and n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, $C_{9-12}$ and the like; similarly, n-membered to n+m-membered means that the number of atoms arranged on the ring is n to n+m, for example, 3- to 12-membered ring means 3-membered ring, 4-membered ring, 5-membered ring, 6-membered ring, 7-membered ring, 8-membered ring, 9-membered ring, 10-membered ring, 11-membered ring and 12-membered ring, and also includes any one of the ranges between n and n+m, for example, 3- to 12-membered ring includes 3- to 6-membered, 3- to 9-membered, 5- to 6-membered, 5- to 7-membered, 6- to 7-membered, 6- to 8-membered, 6- to 10-membered ring and the like.

The term "leaving group" refers to a functional group or atom which can be replaced with another functional group or atom through a substitution reaction (such as nucleophilic substitution reaction). For example, representative leaving groups include triflate; chlorine, bromine and iodine; sulfonate, such as mesylate, tosylate, p-bromobenzenesulfonate, p-toluenesulfonate and the like; acyloxy, such as acetoxy, trifluoroacetoxy and the like.

The term "protecting group" includes, but not limited to "amino protecting group", "hydroxyl protecting group" or "thiol protecting group". The term "amino protecting group" refers to a protecting group suitable for blocking the side reaction on the nitrogen atom of an amino group. Representative amino protecting groups include, but not limited to, formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl)methyl; silyl such as trimethylsilyl (TMS) and tert-butyldimethylsilyl (TBS) and the like. The term "hydroxyl protecting group" refers to a protecting group suitable for blocking the side reaction on a hydroxyl group. Representative hydroxyl protecting groups include, but not limited to, alkyl such as methyl, ethyl and tert-butyl; acyl such as alkanoyl (e.g., acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyldimethylsilyl (TBS) and the like.

The compound of the present disclosure can be prepared by a variety of synthetic methods well known to those skilled in the art, including the following enumerative embodiments, embodiments formed by the following enumerative embodiments in combination with other chemical synthesis methods and equivalent replacements well known to those skilled in the art. The preferred embodiments includes, but not limited to the embodiments of the present disclosure.

All of the solvents used in the present disclosure are commercially available. The present disclosure adopts the abbreviating words as follows: "aq" refers to water; "HATU" refers to O-(7-azabenzotriazol-1-yl)-N,N,N',N'-tetramethyluronium hexafluorophosphate; "EDC" refers to N-(3-dimethylaminopropyl)-N'-ethylcarbodiimide hydrochloride; "m-CPBA" refers to 3-chloroperoxybenzoic acid; "eq" refers to equivalent; "CDI" refers to carbonyldiimidazole; "DCM" refers to dichloromethane; "PE" refers to petroleum ether; "DIAD" refers to diisopropyl azodicarboxylate; "DMF" refers to N,N-dimethylformamide; "DMSO" refers to dimethyl sulfoxide; "EtOAc" refers to ethyl acetate; "EtOH" refers to ethanol; "MeOH" refers to methanol; "CBz" refers to benzyloxycarbonyl, which is an amine protecting group; "BOC" refers to tert-butoxycarbonyl, which is an amine protecting group; "HOAc" refers to acetic acid; "NaCNBH$_3$" refers to sodium cyanoborohydride; "r.t." refers to room temperature; "O/N" refers to overnight; "THF" refers to tetrahydrofuran; "Boc$_2$O" refers to di-tert-butyldicarbonate; "TFA" refers to trifluoroacetic acid; "DIPEA" refers to diisopropylethylamine; "SOCl$_2$" refers to thionyl chloride; "CS$_2$" refers to carbon disulfide; "TsOH" refers to p-toluenesulfonic acid; "NFSI" refers to N-fluoro-N-(phenyl sulfonyl)benzenesulfonamide; "NCS" refers to 1-chloropyrrolidine-2,5-dione; "n-Bu$_4$NF" refers to tetrabutylammonium fluoride; "iPrOH" refers to 2-propanol; "mp" refers to melting point; "LDA" refers to lithium diisopropylamide; Pd(dppf)Cl$_2$ refers to[1,1'-bis(diphenylphosphino)ferrocene]dichloropalladium(II); EDCI refers to 1-ethyl-3-(3-dimethylaminopropyl)carbodiimide hydrochloride; DIEA refers to N,N-diisopropylethylamine; IPA refers to isopropanol; HOBt refers to 1-hydroxybenzotriazole; LiHMDS refers tolithium bis(trimethylsilyl)amide; TEA refers to triethylamine; HEPES refers to 4-hydroxyethylpiperazineethanesulfonic acid.

Compounds are named manually or by ChemDraw® software, and the commercially available compounds use their vendor directory names.

DETAILED DESCRIPTION OF THE PREFERRED EMBODIMENT

Figure 1:
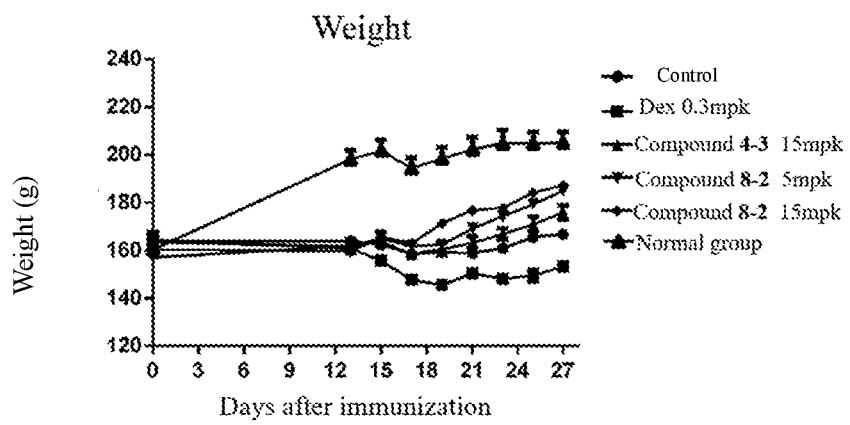
FIG. 1: Body weight changes in arthritis rats.

The following examples further illustrate the present disclosure, but the present disclosure is not limited thereto. The present disclosure has been described in detail in the text, and its specific embodiments have also been disclosed, for one skilled in the art, it is obvious to modify and improve the embodiments of the present disclosure within the spirit and scope of the present disclosure.

Embodiment 1

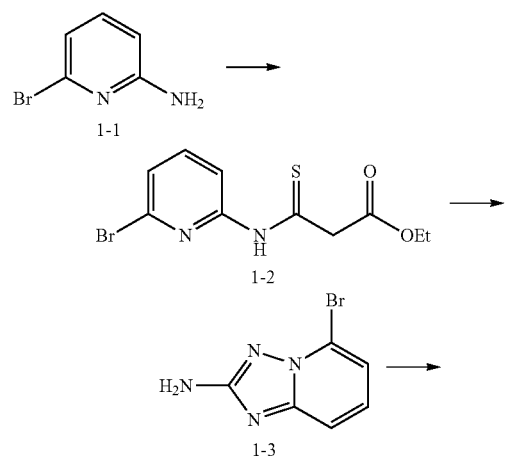

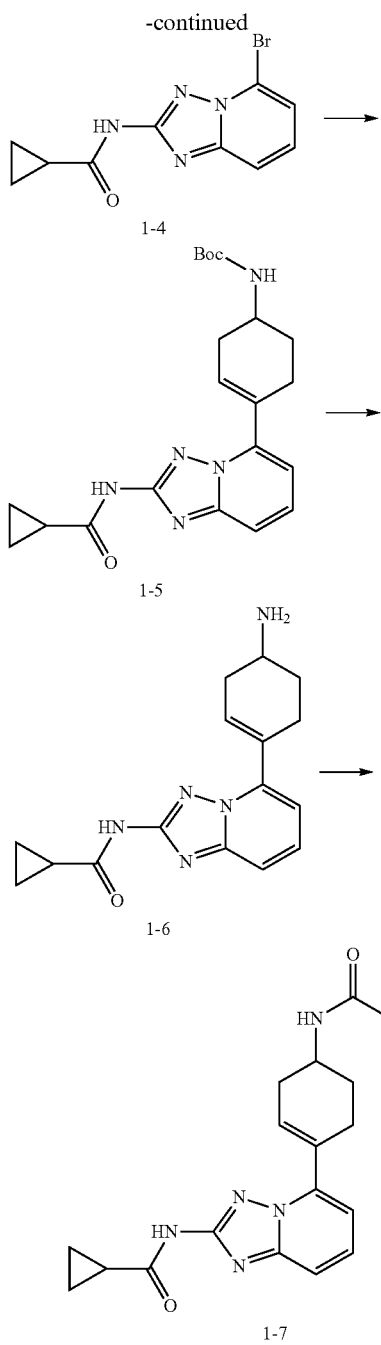

Step 1: Preparation of Compound 1-2

Ethyl isothiocyanate (25.0 g, 190.7 mmol) was slowly added dropwise to a solution of 6-bromopyridin-2-amine (30 g, 173.4 mmol) in dichloromethane (400 mL), and after the addition, the mixture was reacted for 16 hours at 25° C. After TLC monitoring showed that the reaction was completed, the reaction solution was distilled under reduced pressure, and the residue was washed and stirred with 200 mL of petroleum ether for 30 minutes, filtered, and the filter cake was collected and dried to obtain compound 1-2. $^1$H NMR (400 MHz, DMSO-d$_6$) δ=12.17 (s, 1H), 11.66 (br. s., 1H), 8.65 (d, J=7.54 Hz, 1H), 7.82 (t, J=7.92 Hz, 1H), 7.49 (d, J=7.78 Hz, 1H), 4.22 (q, J=7.18 Hz, 2H), 1.25 (t, J=7.16 Hz, 3H). LCMS (ESI) m/z: 304 [M+H]$^+$.

Step 2: Preparation of Compound 1-3

Hydroxylamine hydrochloride (35.2 g, 503.1 mmol) and diisopropylethylamine (54.1 g, 419.3 mmol) were dissolved in a mixed solvent of ethanol (500 mL) and methanol (500 mL), the mixture was stirred at 25° C. for 1 hour, then compound 1-2 (51.0 g, 167.7 mmol) was added. The reaction system was purged with nitrogen three times, heated to 80° C., reacted for 3 hours, and cooled. After TLC monitoring showed that the reaction was completed, the reaction solution was distilled under reduced pressure, and the residue was washed and stirred with water (500 mL) for 10 minutes, filtered, and the filter cake was collected and dried to obtain compound 1-3. $^1$H NMR (400 MHz, DMSO-d$_6$) δ=7.30-7.39 (m, 1H), 7.20 (dd, J=6.78, 1.76 Hz, 1H), 6.27 (s, 2H). LCMS (ESI) m/z: 215 [M+H]$^+$.

Step 3: Preparation of Compound 1-4

At 0° C., cyclopropylformyl chloride (8.8 g, 84.5 mmol) was slowly added dropwise to acetonitrile (150 mL) in which compound 1-3 (15.0 g, 70.4 mmol and triethylamine (21.4 g, 211.2 mmol)) were dissolved. After the addition, the reaction temperature was raised to room temperature and the mixture was reacted for 16 hours. After TLC monitoring showed the raw material was completely consumed, the reaction solution was distilled under reduced pressure, and the residue was dissolved in methylamine alcohol (150 mL) solution, the mixture was heated to 80° C. and reacted for 1 hour, cooled, distilled under reduced pressure to obtain the residue again, the residue was dissolved in a mixture of water (100 mL) and ethyl acetate (200 mL), partitioned, the organic phases were combined and dried over anhydrous sodium sulfate, filtered, the filtrate was distilled under reduced pressure to obtain crude product. The crude product was purified by silica gel column chromatography (ethyl acetate/petroleum ether=0-70% elution) to obtain compound 1-4. $^1$H NMR (400 MHz, DMSO-d$_6$) δ=11.20 (br. s., 1H), 7.68-7.73 (m, 1H), 7.52-7.58 (m, 1 H), 7.46-7.51 (m, 1H), 1.96-2.09 (m, 1H), 0.82 (d, J=6.28 Hz, 4H). LCMS (ESI) m/z: 282 [M+H]$^+$.

Step 4: Preparation of Compound 1-5

A system consisted with a mixed solution of dioxane (120 mL) and water (30 mL) in which N-[4-(4,4,5,5-tetramethyl-1,3,2-dioxaborolan-2-yl)cyclohex-3-en-1-yl]amino carbamic acid tert-butyl ester (11 g, 34.0 mmol), compound 1-4 (7.6 g, 27.2 mmol), K$_2$CO$_3$ (14.11 g, 102.09 mmol) and Pd(dppf)Cl$_2$ (2.49 g, 3.4 mmol) were dissolved was purged 3 times with nitrogen. The mixed solution was stirred at 90° C. for 1.5 hours under nitrogen atmosphere. After TLC monitoring showed the raw material was completely consumed, and the target molecular peak was detected. The reaction solution was concentrated under reduced pressure, then dispersed in 100 mL water, and extracted with ethyl acetate ((150 mL*3)). The organic phases were combined and dried over anhydrous sodium sulfate, filtered, and the filtrate was distilled under reduced pressure to obtain crude product. The crude product was purified by silica gel column chromatography (ethyl acetate/petroleum ether=20-70% elution) to obtain compound 1-5. LCMS (ESI) m/z: 398 [M+H]$^+$.

Step 5: Preparation of Compound 1-6

A solution of compound 1-5 (12 g, 30.2 mmol) and trifluoroacetic acid (13.8 g, 120.8 mmol, 8.9 mL) in dichloromethane (120 mL) was stirred at 25° C. for 5 hours. LCMS showed that the raw material was completely consumed, and the target molecular ion peak was detected. The reaction solution was concentrated under reduced pressure, and the residue was adjusted to pH=8 with saturated sodium bicarbonate solution, and extracted with dichloromethane:methanol (5:1, 200 mL*3). The organic phases were combined and concentrated under reduced pressure to obtain compound 1-6, which was directly used in the next reaction without purification. LCMS (ESI) m/z: 298 [M+H]+.

Step 6: Preparation of Compound 1-7

EDCI (967 mg, 5.04 mmol), HOBt (682 mg, 5.04 mmol), DIEA (1.3 g, 10.1 mmol, 1.8 mL) and compound 1-6 (1 g, 3.36 mmol) were separately added to a solution of 2,2-difluorocyclopropane-carboxylic acid (492 mg, 4.04 mmol) in DMF (30 mL). The mixture was stirred at 25° C. for 12 hours. LCMS showed that the raw material was consumed and the target molecular peak was detected. 60 mL Water was added to the reaction mixture, and the mixture was extracted with ethyl acetate (60 mL*3). The organic phases were combined, washed with saturated brine, dried over sodium sulfate, filtered and concentrated to obtain a crude product. The crude product was isolated by preparation to obtain compound 1-7. $^1$H NMR (400 MHz, METHANOL-$d_4$) δ0.93 (dq, J=7.43, 3.63 Hz, 2H), 1.01-1.09 (m, 2H), 1.68-1.92 (m, 2H), 2.02 (td, J=13.24, 7.65 Hz, 2H), 2.21-2.34 (m, 1H), 2.50-2.87 (m, 4H), 4.11-4.23 (m, 1H), 4.59 (s, 1H), 4.55-4.65 (m, 1H), 6.58-6.67 (m, 1H), 7.06 (d, J=7.28 Hz, 1H), 7.52-7.57 (m, 1H), 7.60-7.67 (m, 1H). LCMS (ESI) m/z: 402 [M+H]+.

1-8

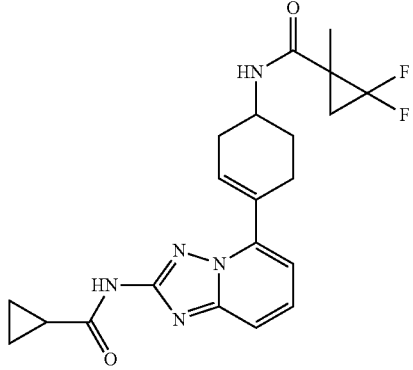

1-9 or 1-10

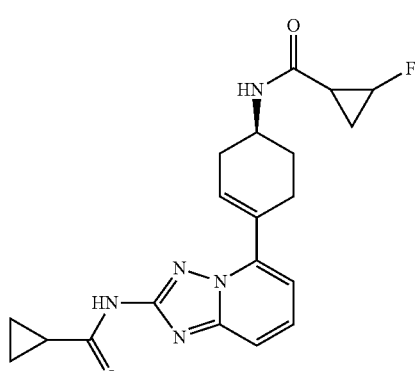

1-9 or 1-10

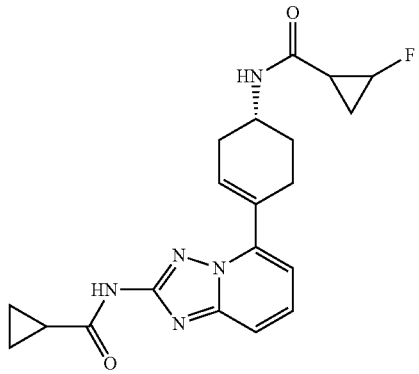

1-11

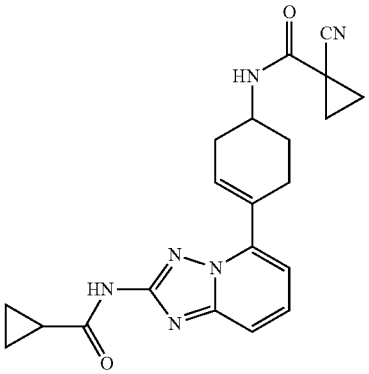

1-12

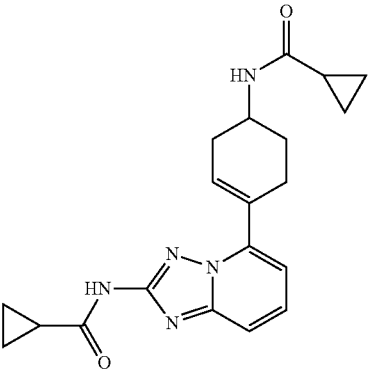

Compound 1-6 was a common intermediate, using the same amide condensation synthesis method used in the preparation of compound 1-7 to prepare (cyclopropylcarboxylic acid differently substituted from that used in the preparation of compound 1-7 was added) the following compound 1-8, 1-9, 1-10, 1-11, 1-12. The characterization data for compounds 1-8, 1-9, 1-10, 1-11, 1-12 were as follows:

Compound 1-8: $^1$H NMR (400 MHz, DMSO-$d_6$) δ 0.72-0.92 (m, 4H), 1.33-1.50 (m, 4H), 1.68 (td, J=11.73, 5.14 Hz, 1H), 1.83-2.11 (m, 3H), 2.27 (br s, 1H), 2.57-2.86 (m, 3H), 3.83-4.02 (m, 1H), 3.83-4.02 (m, 1H), 6.68-6.83 (m, 1H), 7.04 (dd, J=6.15, 2.13 Hz, 1H), 7.53-7.66 (m, 2H), 8.04 (br dd, J=7.28, 5.02 Hz, 1H), 11.01 (br s, 1H). LCMS (ESI) m/z: 416 [M+H]+.

Compound 1-9: $^1$H NMR (400 MHz, DMSO-$d_6$) δ 0.75-0.88 (m, 4H), 0.95-1.07 (m, 1H), 1.44-2.28 (m, 7H), 2.58-2.86 (m, 2H), 3.94 (br d, J=2.51 Hz, 1H), 4.63-5.01 (m, 1H), 6.78 (br s, 1H), 7.05 (br d, J=6.02 Hz, 1H), 7.49-7.71 (m, 2H), 8.07-8.25 (m, 1H), 11.02 (br s, 1H). LCMS (ESI) m/z: 384 [M+H]⁺.

Compound 1-10: ¹H NMR (400 MHz, DMSO-d₆) δ 0.82 (br s, 4H), 1.10 (br dd, J=12.55, 6.27 Hz, 1H), 1.27-1.45 (m, 1H), 1.65 (br d, J=2.76 Hz, 1H), 1.85-2.35 (m, 4H), 2.59-2.82 (m, 1H), 3.91 (br d, J=2.01 Hz, 1H), 4.60-4.94 (m, 1H), 6.78 (br s, 1H), 7.05 (br d, J=4.52 Hz, 1H), 7.59 (br s, 2H), 8.34 (br d, J=7.03 Hz, 1H), 11.03 (br s, 1H), 10.91-11.15 (m, 1H). LCMS (ESI) m/z: 384 [M+H]⁺.

Compound 1-11: ¹H NMR (400 MHz, DMSO-d₆) δ 0.75-0.87 (m, 4H), 1.47-1.60 (m, 4H), 1.68-1.94 (m, 2H), 1.96-2.07 (m, 1H), 2.32-2.45 (m, 2H), 2.57-2.82 (m, 2H), 2.57-2.82 (m, 1H), 3.83-4.06 (m, 1H), 6.74 (br s, 1H), 7.04 (dd, J=5.90, 2.38 Hz, 1H), 7.51-7.67 (m, 2H), 8.12 (br d, J=7.78 Hz, 1H), 11.02 (br s, 1H), 10.95-11.11 (m, 1H). LCMS (ESI) m/z: 391 [M+H]⁺.

Compound 1-12: ¹H NMR (400 MHz, DMSO-d₆) δ 0.59-0.73 (m, 4H), 0.78-0.90 (m, 4H), 1.51-1.71 (m, 2H), 1.86-2.25 (m, 3H), 2.57-2.84 (m, 3H), 3.92 (br d, J=3.26 Hz, 1H), 6.78 (br s, 1H), 7.06 (dd, J=6.27, 2.01 Hz, 1H), 7.49-7.70 (m, 2H), 8.15 (br d, J=7.53 Hz, 1H), 11.04 (br s, 1H). LCMS (ESI) m/z: 366 [M+H]⁺.

Embodiment 2

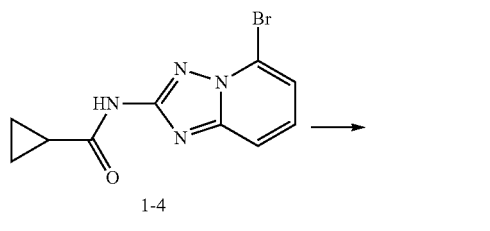

1-4

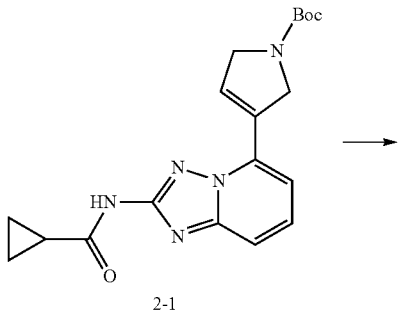

2-1

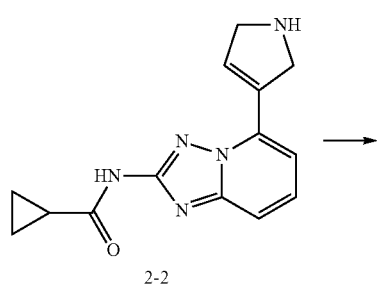

2-2

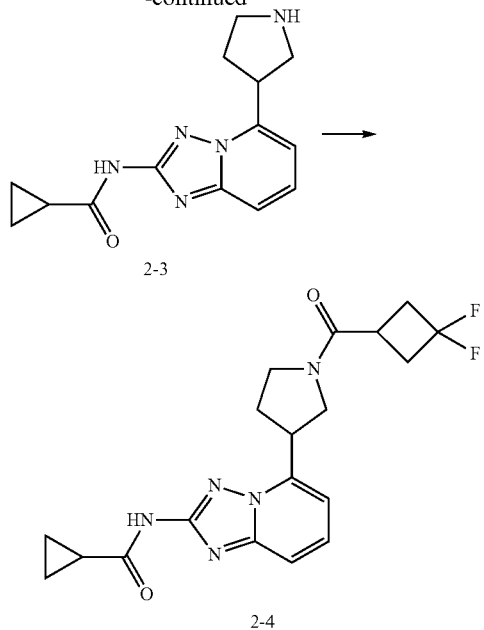

Step 1: Preparation of Compound 2-1

A system consisted with a mixed solution of dioxane (12 mL) and water (3 mL) in which 3-(4,4,5,5-tetramethyl-1,3,2-dioxaborolan-2-yl)-2,5-dihydropyrrole-1-carboxylic acid tert-butyl ester (0.3 g, 1.02 mmol), compound 1-4 (300 mg, 1.07 mmol), K₂CO₃ (421.39 mg, 3.05 mmol) and Pd(dppf)Cl₂ (74.36 mg, 101.63 umol) were dissolved, was purged 3 times with nitrogen. And the mixture was stirred at 90° C. for 2 hours under nitrogen atmosphere. LCMS showed that the raw material was completely consumed, and the target molecular ion peak was detected. The reaction solution was concentrated to dryness under reduced pressure, and separated by silica gel column chromatography to obtain compound 2-1. LCMS (ESI) m/z: 370 [M+H]⁺.

Step 2: Preparation of compound 2-2

A solution of compound 2-1 (0.46 g, 1.25 mmol) and trifluoroacetic acid (3.08 g, 27.01 mmol, 2 mL) in dichloromethane (8 mL) was stirred at 25° C. for 0.5 hour. LCMS showed that the raw material was completely consumed, and the target molecular peak was detected. The reaction solution was concentrated under reduced pressure to obtain crude compound 2-2. The product was used in the next step without purification. LCMS (ESI) m/z: 270 [M+H]⁺.

Step 3: Preparation of compound 2-3

Pd/C (10%, 0.01 g) was added to a solution of compound 2-2 (0.05 g, 185.67 mol) in methanol (10 mL) under argon atmosphere. The mixture was purged 3 times with hydrogen, and then stirred under hydrogen atmosphere (30 psi) at 25° C. for 2 hours. LCMS showed that the raw material was completely consumed, and the target molecular ion peak was detected. The reaction solution was filtered and concentrated to obtain compound 2-3, which was directly used in the next reaction without purification. LCMS (ESI) m/z: 272 [M+H]⁺.

Step 4: Preparation of compound 2-4

EDCI (106 mg, 552.7 μmol), HOBt (75 mg, 552.9 μmol), DIEA (160.50 μL, 921.4 μmol), and compound 2-3 (50 mg, 184.3 μmol) were added to a solution of 3,3-difluorocyclobutane-carboxylic acid (25.08 mg, 184.29 μmol) in DMF (3 mL). The mixture was stirred at 25° C. for 12 hours.

LCMS showed that the raw material was completely consumed, and the target molecular ion peak was detected. 10 mL Water was added to the reaction system to quench the reaction, and the mixture was extracted with ethyl acetate (15 mL*3). The organic phases were combined, washed with saturated brine, dried over sodium sulfate, filtered and concentrated to obtain a crude product. The crude product was separated and purified by preparative HPLC to obtain compound 2-4. $^1$H NMR (400 MHz, DMSO-d$_6$) δ 0.76-0.90 (m, 4H), 1.24 (br s, 2H), 1.94-2.30 (m, 2H), 2.70-2.87 (m, 4H), 3.07-3.28 (m, 1H), 3.54-3.68 (m, 3H), 3.95-4.13 (m, 1H), 3.95-4.16 (m, 1H), 6.96-7.13 (m, 1H), 7.51-7.71 (m, 1H), 7.54-7.69 (m, 1H), 7.54-7.69 (m, 1H), 11.06 (br s, 1H). LCMS (ESI) m/z: 390 [M+H]$^+$.

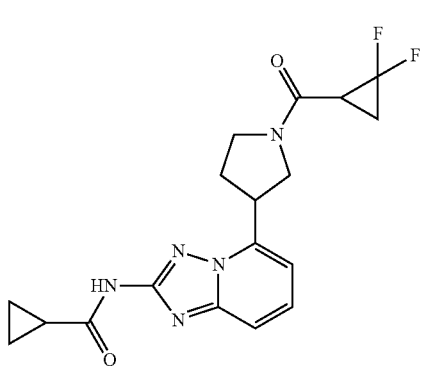

2-5

Compound 2-3 was a common intermediate, using the same synthetic method of amide condensation used in the preparation of compound 2-4 (cyclopropylcarboxylic acid differently substituted from that used in the preparation of compound 2-4 was added) to prepare compound 2-5, the characterization data was as follows:

Compound 2-5: $^1$H NMR (400 MHz, DMSO-d$_6$) δ 0.75-0.90 (m, 4H), 1.77-2.48 (m, 5H), 2.89-3.10 (m, 1H), 3.41-4.36 (m, 5H), 6.93-7.19 (m, 1H), 7.52-7.72 (m, 2H), 11.07 (br s, 1H). LCMS (ESI) m/z: 376 [M+H]$^+$.

Embodiment 3

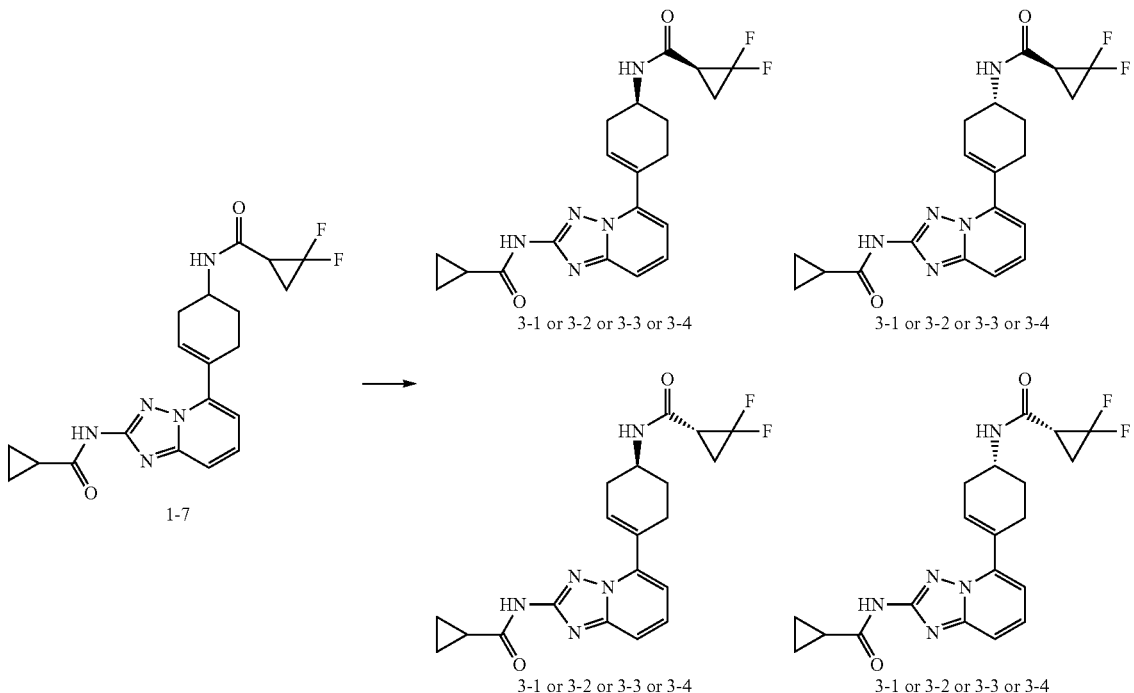 [SMILES: O=C(Nc1nc2cccc(C3=CCC(NC(=O)C4CC4(F)F)CC3)n2n1)C1CC1 ; O=C(Nc1nc2cccc(C3=CC[C@@H](NC(=O)[C@@H]4CC4(F)F)CC3)n2n1)C1CC1 ; O=C(Nc1nc2cccc(C3=CC[C@@H](NC(=O)[C@H]4CC4(F)F)CC3)n2n1)C1CC1 ; O=C(Nc1nc2cccc(C3=CC[C@H](NC(=O)[C@@H]4CC4(F)F)CC3)n2n1)C1CC1 ; O=C(Nc1nc2cccc(C3=CC[C@H](NC(=O)[C@H]4CC4(F)F)CC3)n2n1)C1CC1]

Step 1: Racemic compounds 1-7 (100 mg, 249.1 mol) was subject to chiral separation (SFC separation conditions: column: Chiralpak AS-H 250*30 mm ID, 5 μm; mobile phase: [0.1% NH$_3$H$_2$O IPA]; B %: 35%-35%; flow rate: 50 mL/min; column temperature: 38° C.; wavelength: 220 nm; nozzle pressure: 100 Bar; nozzle temperature: 60° C.; evaporator temperature: 20° C.) to obtain 4 isomers which are compound 3-1, 3-2, 3-3, 3-4.

Compound 3-1, retention time: 4.701 minutes; $^1$HNMR (400 MHz, METHANOL-d$_4$) δ 0.78-1.02 (m, 4H), 1.58-2.00 (m, 5H), 2.10-2.23 (m, 1H), 2.41-2.77 (m, 4H), 4.00-4.12 (m, 1H), 6.50 (br s, 1H), 6.94 (br d, J=6.78 Hz, 1H), 7.40-7.47 (m, 1H), 7.48-7.56 (m, 1H), LCMS (ESI) m/z: 402 [M+H]$^+$.

Compound 3-2, retention time: 4.842 minutes; $^1$HNMR (400 MHz, METHANOL-d$_4$) δ 0.77-0.97 (m, 4H), 1.59-1.99 (m, 5H), 2.16 (ddd, J=18.38, 8.09, 2.64 Hz, 1H), 2.40-2.72 (m, 4H), 4.00-4.09 (m, 1H), 6.53 (br s, 1H), 6.94 (br d, J=7.28 Hz, 1H), 7.39-7.46 (m, 1H), 7.48-7.55 (m, 1H), LCMS (ESI) m/z: 402 [M+H]$^+$.

Compound 3-3, retention time: 5.197 minutes; $^1$HNMR (400 MHz, METHANOL-d$_4$) δ 0.79-1.02 (m, 4H), 1.59-1.99 (m, 5H), 2.16 (ddd, J=18.38, 8.09, 2.64 Hz, 1H), 2.41-2.72 (m, 4H), 4.02-4.09 (m, 1H), 6.53 (br s, 1H), 6.94 (br d, J=7.28 Hz, 1H), 7.40-7.46 (m, 1H), 7.48-7.55 (m, 1H), LCMS (ESI) m/z: 402 [M+H]$^+$.

Compound 3-4, retention time: 6.016 minutes. $^1$HNMR (400 MHz, METHANOL-d$_4$) δ 0.77-0.97 (m, 4H), 1.59-2.01 (m, 5H), 2.16 (ddd, J=18.38, 8.09, 2.64 Hz, 1H), 2.40-2.72 (m, 4H), 4.00-4.10 (m, 1H), 6.53 (br s, 1H), 6.94 (br d, J=7.28 Hz, 1H), 7.39-7.46 (m, 1H), 7.48-7.55 (m, 1H), LCMS (ESI) m/z: 402 [M+H]+.

Embodiment 4

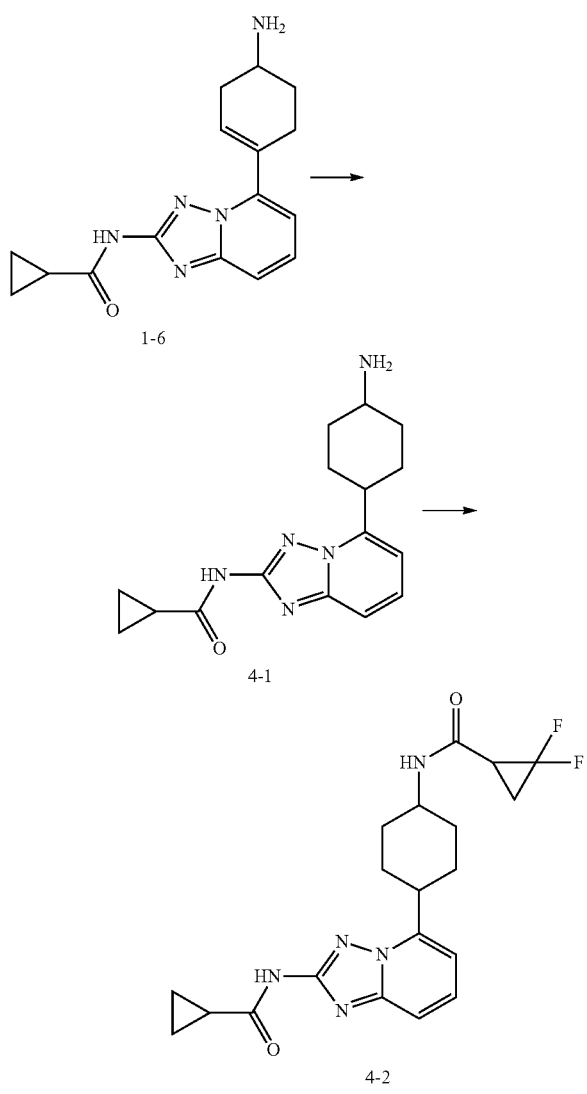

Step 1: Preparation of Compound 4-1

Pd/C (14 mg, 10% content) was added to a solution of compound 1-6 (0.14 g, 470.8 μmol) in methanol (15 mL) under argon atmosphere. The suspension was purged 3 times with hydrogen, and then the mixture was stirred under hydrogen atmosphere (30 psi) at 25° C. for 2 hours. LCMS showed that the raw material was completely consumed, and the target molecular ion peak was detected. The reaction solution was filtered and concentrated to obtain compound 4-1, which was directly used in the next reaction without purification. LCMS (ESI) m/z: 300 [M+H]+.

Step 2: Preparation of Compound 4-2

EDCI (134.5 mg, 701.5 μmol), HOBt (94.8 mg, 701.5 μmol), DIEA (181.3 mg, 1.40 mmol, 244.8 μL) and compound 4-1 (140 mg, 467.7 mol) were added to a solution of 2,2-difluorocyclopropanecarboxylic acid (62.79 mg, 514.41 μmol) in DMF (5 mL). The mixture was stirred at 25° C. for 12 hours. LCMS showed that the raw material was completely consumed, and the target molecular ion peak was detected. The reaction solution was concentrated to dryness under reduced pressure, and separated and purified by preparative HPLC to obtain compound 4-2. ¹H NMR (400 MHz, DMSO-d₆) δ 0.76-0.89 (m, 4H), 1.38 (br d, J=11.80 Hz, 1H), 1.56-2.17 (m, 11H), 2.29-2.34 (m, 1H), 2.62-2.82 (m, 1H), 3.63-4.15 (m, 1H), 7.00 (d, J=7.03 Hz, 1H), 7.51-7.68 (m, 2H), 8.30 (br d, J=7.78 Hz, 1H), 11.02 (br d, J=9.79 Hz, 1H). LCMS (ESI) m/z: 404 [M+H]+.

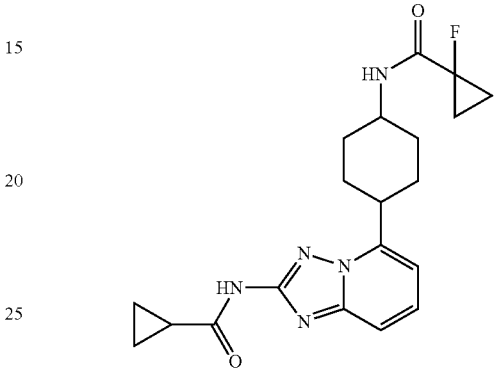

Common intermediate 4-1 was used as the starting material, using the same synthetic method of amide condensation used in the preparation of compound 4-2 (cyclopropylcarboxylic acid differently substituted from that used in the preparation of compound 4-2 was added) to prepare compound 4-3, the characterization data was as follows:

¹H NMR (400 MHz, DMSO-d₆) δ 0.68-0.91 (m, 4H), 1.08-1.40 (m, 4H), 1.52-1.78 (m, 3H), 1.80-2.18 (m, 6H), 3.43 (br s, 1H), 4.11 (br d, J=3.51 Hz, 1H), 6.88-7.19 (m, 1H), 7.45-7.75 (m, 2H), 7.95-8.43 (m, 1H), 11.03 (br d, J=8.03 Hz, 1H). LCMS (ESI) m/z: 386 [M+H]+.

Embodiment 5

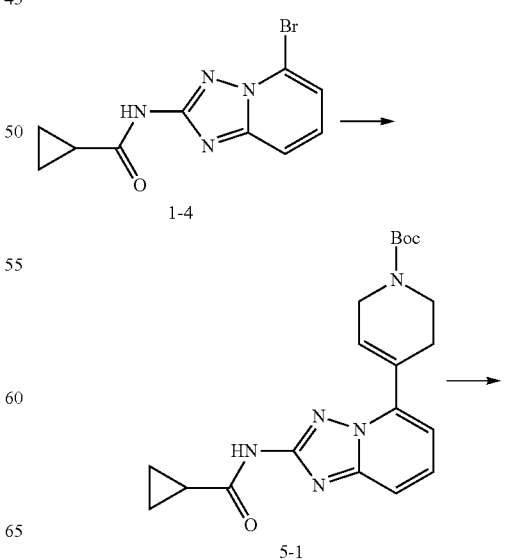

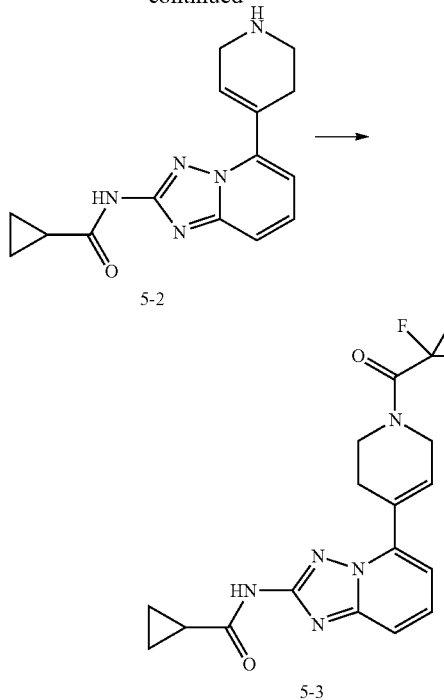

5-2

5-3

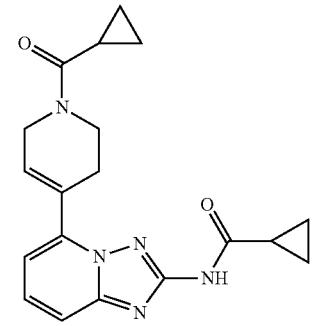

5-4

Common intermediate 5-2 was used as the starting material, using the same synthetic method of amide condensation used in the preparation of compound 5-3 (cyclopropylcarboxylic acid differently substituted from that used in the preparation of compound 5-3 was added) to prepare compound 5-4, the characterization data was as follows:

$^1$H NMR (400 MHz, DMSO-d$_6$) δ 0.65-0.93 (m, 8H), 1.92-2.18 (m, 2H), 1.92-2.18 (m, 1H), 2.57-2.88 (m, 2H), 3.72 (br s, 1H), 3.93 (br s, 1H), 4.23 (br s, 1H), 4.51 (br s, 1H), 6.88-7.20 (m, 1H), 7.11 (br s, 1H), 7.52-7.76 (m, 2H), 11.07 (br s, 1H). LCMS (ESI) m/z: 352 [M+H]$^+$.

Embodiment 6

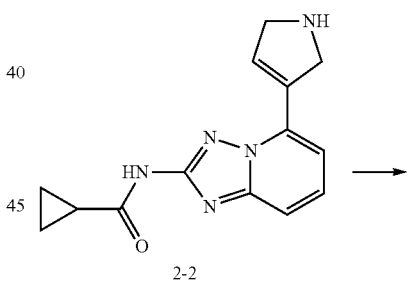

2-2

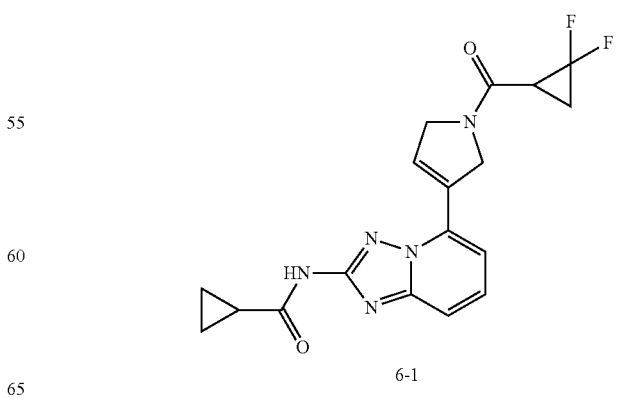

6-1

Step 1: Preparation of Compound 5-1

A system consisted with a mixed solution of dioxane (20 mL) and water (5 mL) in which compound 1-4 (1 g, 3.56 mmol), (4,4,5,5-tetramethyl-1,3,2-dioxaborolane-2-yl)-3,6-dihydro-2H-pyridine-1-carboxylic acid tert-butyl ester (1.2 g, 3.9 mmol), Pd(dppf)Cl$_2$.CH$_2$Cl$_2$ (291 mg, 355.7 mol) and K$_2$CO$_3$ (1.47 g, 10.67 mmol) were dissolved, was purged 3 times with nitrogen. The suspension was stirred at 90° C. for 12 hours under nitrogen atmosphere. LCMS showed that the raw material was completely consumed, and the target molecular ion peak was detected. The reaction solution was concentrated under reduced pressure, and the residue was separated and purified by silica gel column chromatography to obtain compound 5-1. LCMS (ESI) m/z: 384 [M+H]$^+$.

Step 2: Preparation of Compound 5-2

A solution of compound 5-1 (1 g, 2.6 mmol) and TFA (7.7 g, 67.5 mmol, 5 mL) in dichloromethane (20 mL) was stirred at 25° C. for 1 hour. LCMS showed that the raw material was completely consumed, and the target molecular ion peak was detected. The reaction solution was concentrated under reduced pressure to obtain compound 5-2, which was directly used in the next reaction without further purification. LCMS (ESI) m/z: 284 [M+H]$^+$.

Step 3: Preparation of Compound 5-3

EDCI (152 mg, 794 μmol), HOBt (107 mg, 794 μmol) and compound 5-2 (150 mg, 529.4 mol) were added to a solution of 1-fluorocyclopropanecarboxylic acid (27.55 mg, 264.71 mol) in DMF (5 mL) and DIEA (205 mg, 1.6 mmol, 277 uμL). The mixture was stirred at 25° C. for 12 hours. LCMS showed that the raw material was completely consumed, and the target molecular ion peak was detected. 10 mL Water was added to quench the reaction, and the mixture was extracted with ethyl acetate (20 mL*3). The organic phases were combined, washed with saturated brine, dried over sodium sulfate, filtered and concentrated to obtain a crude product. The crude product was separated and purified by preparative HPLC to obtain compound 5-3. $^1$H NMR (400 MHz, DMSO-d$_6$) δ 0.75-0.88 (m, 4H), 1.17-1.38 (m, 4H), 2.05 (br d, J=17.32 Hz, 1H), 2.78 (br s, 2H), 3.87 (br s, 2H), 4.27 (br s, 2H), 7.00-7.19 (m, 2H), 7.53-7.74 (m, 2H), 11.07 (br s, 1H). LCMS (ESI) m/z: 370 [M+H]$^+$.

Step 1: Preparation of Compound 6-1

T₃P (249 mg, 391.3 mol, 232 μL) was added to a solution of compound 2-2 (0.1 g, 260.9 mol), 2,2-difluorocyclopropanecarboxylic acid (31.9 mg, 260.9 μmol) in DMF (5 mL) and DIEA (101 mg, 782.6 μmol, 136 uL), and the mixture was stirred at 40° C. for 2 hours. LCMS showed that the raw material was completely consumed, and the target molecular ion peak was detected. The reaction solution was concentrated under reduced pressure, and separated and purified by preparative HPLC to obtain compound 6-1. ¹H NMR (400 MHz, DMSO-d₆) δ 0.73-0.98 (m, 4H), 2.06 (br s, 3H), 3.07 (br d, J=12.76 Hz, 1H), 4.50 (br s, 1H), 4.60-4.78 (m, 2H), 4.90 (br s, 1H), 5.13 (br d, J=13.63 Hz, 1H), 7.16 (br d, J=7.63 Hz, 1H), 7.64-7.76 (m, 2H), 7.78-7.91 (m, 1H), 11.22 (br d, J=4.25 Hz, 1H). LCMS (ESI) m/z: 374 [M+H]⁺.

Common intermediate 2-2 was used as the starting material, using the same synthetic method of amide condensation used in the preparation of compound 6-1 (cyclopropylcarboxylic acid differently substituted from that used in the preparation of compound 6-1 was added) to prepare compound 6-2, the characterization data was as follows:

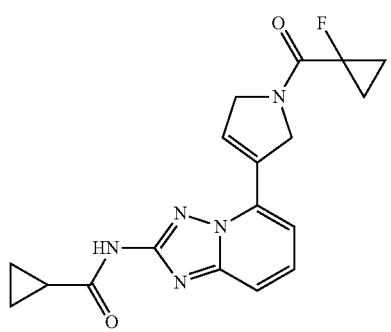
6-2

¹H NMR (400 MHz, DMSO-d₆) δ 0.74-0.95 (m, 4H), 1.22-1.45 (m, 4H), 2.00-2.13 (m, 1H), 4.58 (br d, J=1.50 Hz, 1H), 4.75-4.91 (m, 2H), 5.07 (br s, 1H), 7.07-7.23 (m, 1H), 7.63-7.77 (m, 2H), 7.84 (br d, J=9.51 Hz, 1H), 11.20 (br s, 1H). LCMS (ESI) m/z: 356 [M+H]⁺.

Embodiment 8

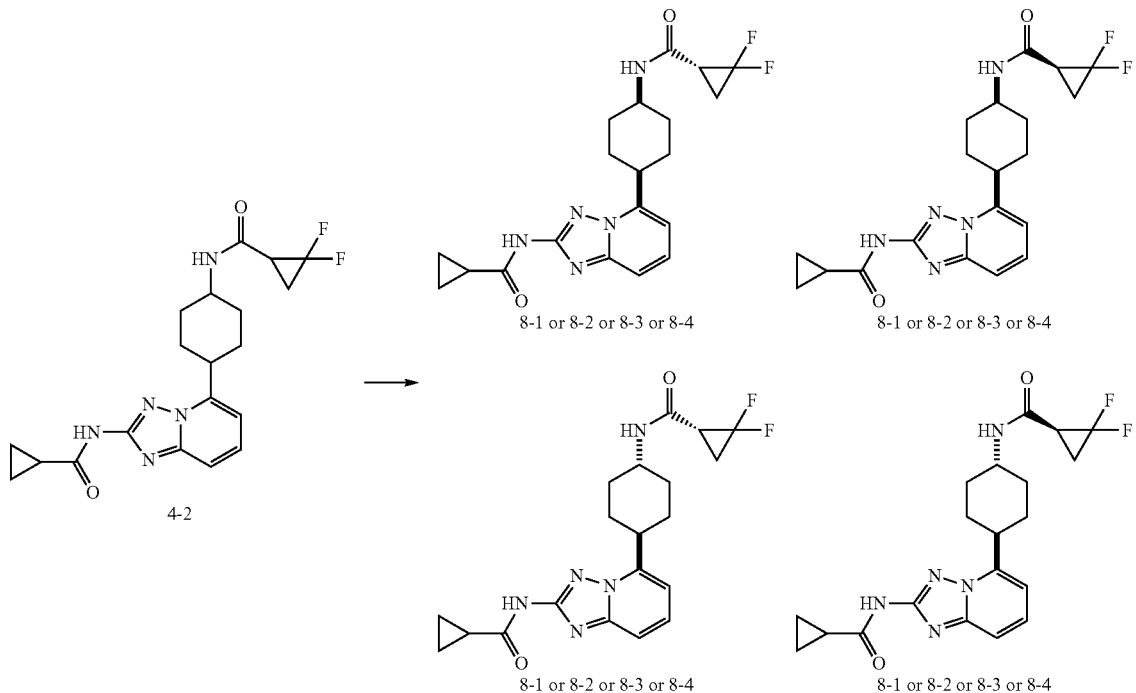

Step 1: Racemic compound 4-2 (100 mg, 247.88 mol) was subject to chiral separation (SFC separation conditions: column: DAICEL CHIRALPAKAD-H (250 mm*30 mm, 5 μm); mobile phase: [0.1% NH$_3$H$_2$O EtOH]; B %: 40%-40%; flow rate: 50 mL/min; column temperature: 38° C.; wavelength: 220 nm; nozzle pressure: 100 Bar; nozzle temperature: 60° C.; evaporator temperature: 20° C.) to obtain 4 isomers.

Compound 8-1, retention time: 5.122 minutes; $^1$H NMR (400 MHz, DMSO-d$_6$) δ 0.65-0.94 (m, 1H), 0.69-0.91 (m, 4H), 1.62-1.96 (m, 11H), 2.74 (ddd, J=14.31, 10.79, 8.28 Hz, 1H), 4.00-4.19 (m, 1H), 7.01 (d, J=7.03 Hz, 1H), 7.44-7.76 (m, 2H), 8.32 (br d, J=7.53 Hz, 1H), 11.04 (br s, 1H). LCMS (ESI) m/z: 404 [M+H]$^+$.

Compound 8-2, retention time: 5.827 minutes; $^1$H NMR (400 MHz, DMSO-d$_6$) δ 0.69-0.92 (m, 5H), 1.63-1.97 (m, 11H), 2.64-2.90 (m, 1H), 3.99-4.21 (m, 1H), 7.01 (d, J=7.28 Hz, 1H), 7.43-7.81 (m, 2H), 8.32 (br d, J=7.53 Hz, 1H), 11.04 (br s, 1H). LCMS (ESI) m/z: 404 [M+H]$^+$.

Compound 8-3, retention time: 6.127 minutes; $^1$H NMR (400 MHz, DMSO-d$_6$) δ 0.68-0.95 (m, 5H), 1.29-1.48 (m, 2H), 1.55-1.71 (m, 2H), 1.75-2.18 (m, 7H), 2.54-2.61 (m, 1H), 3.61-3.79 (m, 1H), 6.99 (br d, J=7.03 Hz, 1H), 7.41-7.75 (m, 2H), 8.34 (br d, J=7.53 Hz, 1H), 11.02 (br s, 1H). LCMS (ESI) m/z: 404 [M+H]$^+$.

Compound 8-4, retention time: 6.323 minutes. $^1$H NMR (400 MHz, DMSO-d$_6$) δ 0.72-0.93 (m, 5H), 1.29-1.47 (m, 2H), 1.55-1.72 (m, 2H), 1.74-2.00 (m, 5H), 2.03-2.16 (m, 3H), 3.69 (br dd, J=7.28, 3.76 Hz, 1H), 7.00 (br d, J=7.03 Hz, 1H), 7.43-7.69 (m, 2H), 8.33 (br d, J=7.53 Hz, 1H), 11.02 (br s, 1H). LCMS (ESI) m/z: 404 [M+H]$^+$.

Embodiment 10

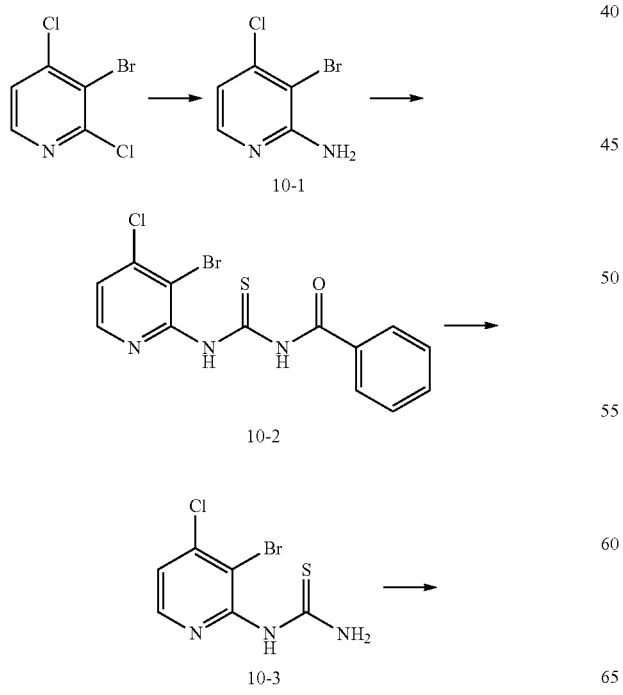

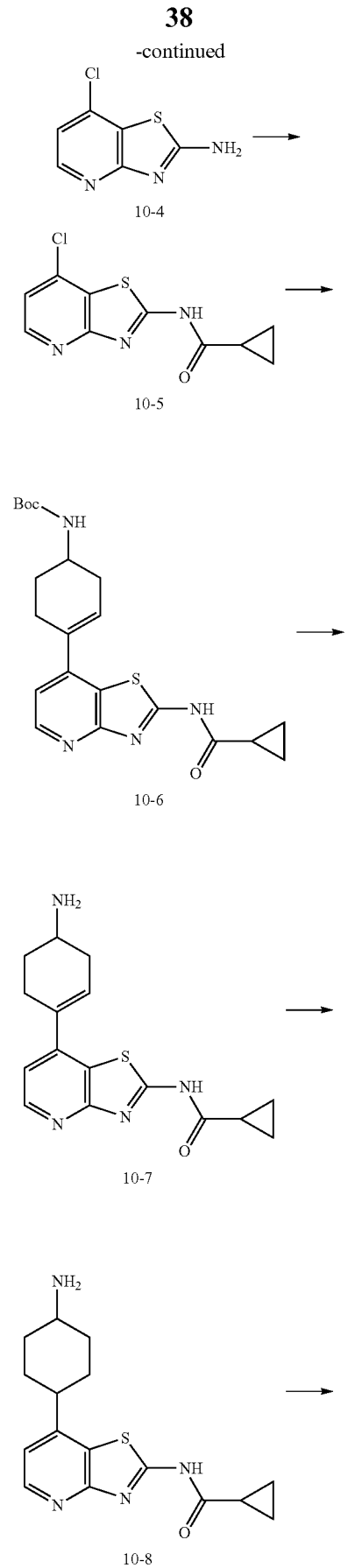

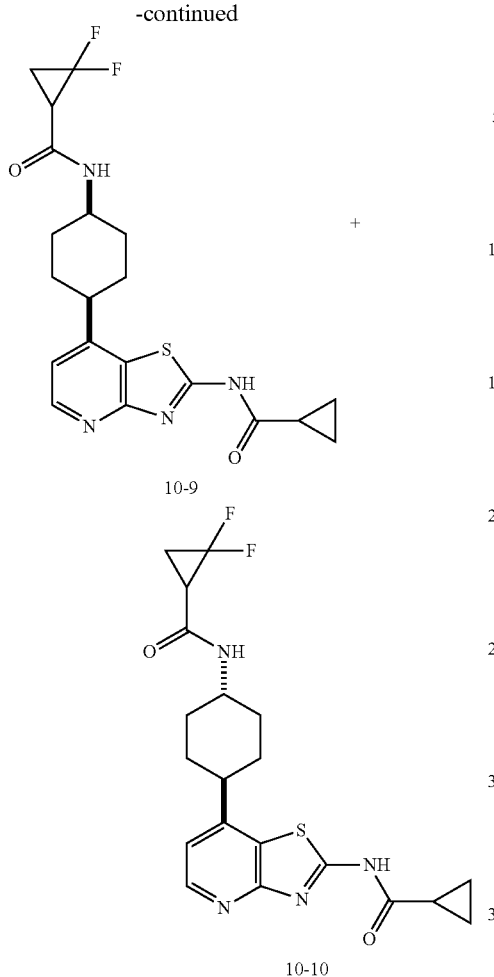

10-9

10-10

Step 1: Preparation of Compound 10-1

Aqueous ammonia (38.8 g, 276.9 mmol, 42.7 mL) in which 3-bromo-2,4-dichloro-pyridine (3.2 g, 14.10 mmol) was dissolved was stirred at 130° C. for 24 hours. The TLC showed that the raw materials were completely consumed and new point was generated. The reaction solution was concentrated under reduced pressure, and separated and purified by silica gel column chromatography to obtain compound 10-1. LCMS (ESI) m/z: 208 [M+H]$^+$.

Step 2: Preparation of Compound 10-2

At 0° C., benzoyl isothiocyanate (3.30 g, 20.25 mmol, 2.73 mL) was added to a solution of compound 10-1 (1.4 g, 6.75 mmol). The mixture was stirred at 25° C. for 12 hours. LCMS showed that the raw material was completely consumed, and the target molecular ion peak was monitored. The reaction solution was concentrated, and the residue was separated and purified by silica gel column chromatography to obtain compound 10-2. LCMS (ESI) m/z: 371 [M+H]$^+$.

Step 3: Preparation of Compound 10-3

NaOH (2M, 10.39 mL) was added dropwise to a solution of compound 10-2 (770 mg, 2.08 mmol) in methanol (0.75 mL). The reaction solution was stirred at 25° C. for 1 hour. LCMS showed that the raw material was completely consumed, and the target molecular ion peak was monitored. The reaction solution was adjusted to pH=6 with diluted hydrochloric acid (1M), and then suction filtered to obtain compound 10-3, which was directly used in the next reaction without further purification. LCMS (ESI) m/z: 268 [M+H]$^+$.

Step 4: Preparation of Compound 10-4

At 0° C., NaH (186 mg, 4.7 mmol, content 60%) was added to a solution of compound 10-3 (400 mg, 1.50 mmol) in DMF (10 mL) in portions. The mixture was stirred at 80° C. for 3 hours. LCMS showed that the raw material was completely consumed, and the target molecular ion peak was detected. At 0° C., the reaction was quenched with 10 mL saturated ammonium chloride solution, and then extracted with ethyl acetate (30 mL*3). The organic phases were combined, washed with saturated brine, dried over sodium sulfate, filtered and concentrated to obtain a crude product. The crude product was separated and purified by column chromatography to obtain compound 10-4. LCMS (ESI) m/z: 186 [M+H]$^+$.

Step 5: Preparation of Compound 10-5

Cyclopropylformyl chloride (198 mg, 1.89 mmol, 172 μL) was added dropwise to a solution of compound 10-4 (70 mg, 377.1 mol) in acetonitrile (15 mL) and TEA (191 mg, 1.89 mmol, 263 uL) at 0° C. The mixture was stirred at 25° C. for 1 hour. LCMS showed that the raw material was completely consumed, and the target molecular ion peak was detected. The reaction solution was concentrated under reduced pressure, quenched by adding 20 mL water, and extracted with DCM:MeOH (20:1, 30 mL*3). The organic phases were combined, washed with saturated brine, dried over sodium sulfate, filtered and concentrated to obtain compound 10-5, which was used in the next reaction without further purification. LCMS (ESI) m/z: 254 [M+H]$^+$.

Step 6: Preparation of Compound 10-6

$K_2CO_3$ (261.48 mg, 1.89 mmol) and Pd(dppf)$C_2 \cdot CH_2Cl_2$ (51.5 mg, 63.1 mol) were added to a solution of compound 10-5 (160 mg, 630.7 μmol) and N-[4-(4,4,5,5-tetramethyl-1,3,2-dioxolane-2-yl)cyclohex-3-en-1-yl)carbamic acid tert-butyl ester (204 mg, 630.6 μmol) in dioxane (12 mL) and water (3 mL). Under the protection of nitrogen, the reaction solution was stirred at 90° C. for 2 hours. LCMS showed that the raw material was completely consumed, and the target molecular ion peak was detected. The reaction solution was filtered and concentrated to remove the solvent. 15 mL Water was added and extracted with DCM:MeOH (20:1, 20 mL*3). The organic phases were combined, washed with saturated brine, dried over sodium sulfate, filtered and concentrated to obtain a crude product. The crude product was separated and purified by silica gel column chromatography to obtain compound 10-6. LCMS (ESI) m/z: 415 [M+H]$^+$.

Step 7: Preparation of Compound 10-7

TFA (3.1 g, 27.0 mmol, 2 mL) was added to a solution of compound 10-6 (160 mg, 386 mol) in dichloromethane (5 mL), and the mixture was stirred at 25° C. for 1 hour. LCMS showed that the raw material was completely consumed, and the target molecular ion peak was detected. The reaction solution was concentrated to obtain compound 10-7, which was used in the next reaction without purification. LCMS (ESI) m/z: 315 [M+H]$^+$.

Step 8: Preparation of Compound 10-8

Pd/C (50 mg, 10% purity) was added to a solution of compound 10-7 (230 mg, 536.85 mol, TFA) in methanol (10 mL) under argon atmosphere. The suspension was purged 3 times with hydrogen. The mixture was stirred at 25° C. for 12 hours under hydrogen atmosphere (30 psi). LCMS showed that the raw material was completely consumed, and the target molecular peak was detected. The reaction solution was filtered and concentrated to obtain compound 10-8. LCMS (ESI) m/z: 317 [M+H]$^+$.

Step 9: Preparation of Compound 10-9

EDCI (218 mg, 1.14 mmol), HOBt (153.73 mg, 1.14 mmol) and 2,2-difluorocyclopropanecarboxylic acid (93 mg, 758.5 μmol, 1 eq) were added to a solution of compound 10-8 (240 mg, 758.5 mol) in DMF (5 mL) and DIEA (294 mg, 2.28 mmol, 396.34 uL). The mixture was stirred at 25° C. for 12 hours. LCMS showed that the raw material was completely consumed, and the target molecular ion peak was detected. The mixture was quenched by adding 20 mL water and extracted with DCM:MeOH (20:1, 30 mL*3). The organic phases were combined, washed with saturated brine, dried over sodium sulfate, filtered and concentrated to obtain a crude product. The crude product was isolated by preparative HPLC to obtain compound 10-9. $^1$H NMR (400 MHz, DMSO-$d_6$) δ 0.92-1.07 (m, 4H), 1.32-1.49 (m, 2H), 1.72-2.09 (m, 10H), 2.79-2.91 (m, 1H), 3.59-3.72 (m, 1H), 7.55 (d, J=5.52 Hz, 1H), 8.32 (br d, J=7.78 Hz, 1H), 8.46 (d, J=5.52 Hz, 1H). LCMS (ESI) m/z: 421 [M+H]$^+$. Compound 10-10. $^1$H NMR (400 MHz, DMSO-$d_6$) δ 0.88-1.11 (m, 4H), 1.62-1.93 (m, 8H), 1.97-2.12 (m, 3H), 2.67-2.83 (m, 1H), 2.93 (br t, J=10.54 Hz, 1H), 3.98 (br d, J=3.26 Hz, 1H), 7.56 (d, J=5.52 Hz, 1H), 8.38 (br d, J=7.03 Hz, 1H), 8.47 (d, J=5.52 Hz, 1H). LCMS (ESI) m/z: 421 [M+H]$^+$.

Biological Activity Assay

Experimental Embodiment 1: In Vitro Activity Assay of JAK1, JAK 2, JAK 3, Tyk2 Kinase Experimental Materials Recombinant human-derived JAK1, JAK2, JAK3, Tyk2 protease, main instruments and reagents were provided by Eurofins in the UK Experimental Method JAK2, JAK3 and TYK2 dilution: 20 mM MOPS, 1 mM EDTA, 0.01% Brij-35.5% glycerol, 0.1% β-mercaptoethanol. 1 mg/mL BSA; JAK1 dilution: 20 mM TRIS, 0.2 mM EDTA, 0.1% β-mercaptoethanol, 0.01% Brij-35.5% glycerol. All compounds were prepared as 100% DMSO solutions, and the concentration of the compound reached 50 times the final measured concentration. The test compound was diluted with a 3-fold concentration gradient, the final concentration was 10 μM to 0.001 μM in total 9 concentrations, and the content of DMSO in the detection reaction was 2%. The working stock solution of the compound was added to the wells as the first component of the reaction, and then the remaining components were added according to the protocol detailed below.

JAK1 (h) Enzyme Reaction

JAK1 (h) was incubated with 20 mM Tris/HCl pH 7.5, 0.2 mM EDTA, 500 μM MGEEPLYWSFPAKKK, 10 mM magnesium acetate and [γ-$^{33}$P]-ATP (activity and concentration were formulated as needed). Mg/ATP mixture was added to initiate the reaction. After incubating at room temperature for 40 minutes, the reaction mixture was added with 0.5% phosphoric acid to stop the reaction. Then 10 μL reaction solution was spotted on a P30 filter pad and washed with 0.425% phosphoric acid three times and methanol once over 4 minutes, dried, and counted scintillation.

JAK2 (h) Enzyme Reaction

JAK2 (h) and 8 mM MOPS pH 7.0, 0.2 mM EDTA, 100M KTFCGTPEYLAPEVRREPRILSEE-EQEMFRDFDYIADWC, 10 mM magnesium acetate and [γ-$^{33}$P]-ATP (activity and concentration were formulated as needed) were incubated together. Mg/ATP mixture was added to initiate the reaction. After incubating at room temperature for 40 minutes, the reaction mixture was added with 0.5% phosphoric acid to stop the reaction. Then 10 L reaction solution was spotted on a P30 filter pad and washed with 0.425% phosphoric acid three times and methanol once over 4 minutes, dried, and counted scintillation.

JAK3 (h) Enzyme Reaction

JAK3 (h) was incubated with 8 mM MOPS pH 7.0, 0.2 mM EDTA, 500 μM GGEEEEYFELVKKKK, 10 mM magnesium acetate and [γ-$^{33}$P]-ATP (activity and concentration were formulated as needed). Mg/ATP mixture was added to initiate the reaction. After incubating at room temperature for 40 minutes, the reaction mixture was added with 0.5% phosphoric acid to stop the reaction. Then 10 μL the reaction solution was spotted on a P30 filter pad and washed with 0.425% phosphoric acid three times and methanol once over 4 minutes, dried, and counted scintillation.

TYK2 (h) Enzyme Reaction

TYK2 (h) was incubated with 8 mM MOPS pH 7.0, 0.2 mM EDTA, 250 μM GGMEDIYFEFMGGKKK, 10 mM magnesium acetate and [γ-$^{33}$P]-ATP (activity and concentration were formulated as needed). Mg/ATP mixture was added to initiate the reaction. After incubating at room temperature for 40 minutes, the reaction mixture was added with 0.5% phosphoric acid to stop the reaction. Then 10 μL reaction was spotted on a P30 filter pad and washed with 0.425% phosphoric acid three times and methanol once over 4 minutes, dried, and counted scintillation.

Data Analysis

The $IC_{50}$ results were analyzed by XLFIT5 (205 formula) of IDBS Company, see Table 1 for details.

TABLE 1

Results of in vitro screening tests of compounds of the present disclosure

| Compound | JAK1 ($IC_{50}$, nM) | JAK2 ($IC_{50}$, nM) | JAK3 ($IC_{50}$, nM) | TYK2 ($IC_{50}$, nM) |
|---|---|---|---|---|
| 1-7 | 20 | 239 | 3114 | 73 |
| 1-8 | 209 | 1159 | >10000 | 729 |
| 1-9 | 186 | 1711 | >10000 | 1003 |
| 1-10 | 40 | 445 | >10000 | 215 |
| 1-11 | 182 | 1383 | >10000 | 1402 |
| 1-12 | 149 | 1419 | >10000 | 497 |
| 3-1 | 12 | 141 | 5518 | 78 |
| 3-2 | 163 | NA | NA | 1369 |
| 3-3 | 166 | NA | NA | 942 |
| 3-4 | 17 | 126 | 2548 | 71 |
| 4-2 | 3 | 23 | 2053 | 10 |
| 4-3 | 31 | 360 | 4380 | 127 |
| 5-3 | 132 | 671 | 4380 | 462 |
| 5-4 | 90 | 422 | >10000 | 178 |
| 6-1 | 70 | 208 | >10000 | 244 |
| 6-2 | 531 | 1121 | >10000 | 2873 |
| 7-3 | 236 | 1332 | >10000 | 778 |
| 8-1 | 111 | 861 | >10000 | 633 |
| 8-2 | 2 | 22 | 957 | 24 |
| 8-3 | 494 | 5771 | >10000 | 3444 |
| 8-4 | 442 | 3747 | >10000 | 2442 |
| 9-5 | 291 | 1287 | 1287 | 1184 |
| 10-9 | 2291 | >10000 | >10000 | 245 |
| 10-10 | 145 | 259 | 1174 | 835 |

Note:
NA means not tested.

Conclusion: The compounds of the present disclosure exhibited good selective inhibitory activity on TYK2 and JAK1 in the in vitro activity assay among four kinase subtypes JAK1, JAK2, JAk3 and TYK2.

Experimental Embodiment 2: Pharmacokinetic (PK) Assay

The clear solution obtained by dissolving the test compound was injected into male mice (C57BL/6) or rats (SD)

by tail vein and gavage respectively (overnight fasting, 7-8 weeks old). After administration of the test compound, blood of the group subjected to the injection by tail vein was collected from the mandibular vein at 0.117, 0.333, 1, 2, 4, 7 and 24 hours and centrifuged, and blood of the group subjected to gavage was collected at 0.25, 0.5, 1, 2, 4, 8 and 24 hours, respectively. The drug concentration on blood was determined by LC-MS/MS, the related pharmacokinetic parameters were calculated by the linear logarithm trapezoid method of non atrioventricular model by WinNonlin™ Version 6.3. The test results were as follows:

TABLE 2-1

PK assay results of compound 1-7 in rat

| PK parameters | Results |
|---|---|
| $T_{1/2}$ (hr) | 2.07 |
| $C_{max}$ (nM) | 23867 |
| $AUC_{0-inf}$ (nM · hr) | 18033 |
| Bioavailability (%)$^a$ | 75.2% |

TABLE 2-2

PK assay results of compound 3-1 in rat

| PK parameters | Results |
|---|---|
| $T_{1/2}$ (hr) | 3.11 |
| $C_{max}$ (nM) | 3800 |
| $AUC_{0-inf}$ (nM · hr) | 19967 |
| Bioavailability (%)$^a$ | 30.0% |

TABLE 2-3

PK assay results of compound 4-2 in rat

| PK parameters | Results |
|---|---|
| $T_{1/2}$ (h) | 2.22 |
| $C_{max}$ (nM) | 13433 |
| $AUC_{0-inf}$ (nM · h) | 11021 |
| Bioavailability (%)$^a$ | 58.6% |

TABLE 2-4

PK assay results of compound 4-3 in rat

| PK parameters | Results |
|---|---|
| $T_{1/2}$ (h) | 2.86 |
| $C_{max}$ (nM) | 24750 |
| $AUC_{0-inf}$ (nM · h) | 85760 |
| Bioavailability (%)$^a$ | 89.8% |

Note:
$T_{1/2}$: half-life;
Cmax: peak concentration;

$AUC_{0-inf}$: the area under the plasma concentration-time curve from 0 hours to infinity;

Bioavailability: Bioavailability.

Conclusion: the compounds of the present disclosure had good oral bioavailability in rat, and higher exposure, which was beneficial for good in vivo medicinal efficacy.

Experimental Embodiment 3

In vivo drug efficacy study in an adjuvant-induced arthritis model (AIA)

Experimental Purpose:

Rheumatoid arthritis is a type of multiple autoimmune diseases, which results in inflammation, injury and deformity of the joints due to autoimmune reactions. In severe cases, it can cause systemic inflammation. The adjuvant-induced arthritis rat model is one of the animal models commonly used in rheumatoid arthritis disease research and new drug development. Its pathogenesis and clinical symptoms are similar to human rheumatoid arthritis diseases. A systemic response was induced by immune cells and antibodies with bone and joint injury functions through injecting tuberculous branch rods via the foot pads in the model, specifically manifested in joint swelling, osteolysis, synovial damage and other symptoms similar to human rheumatoid arthritis.

The purpose of this embodiment is to investigate the therapeutic effects of compounds 4-3 and 8-2 on adjuvant-induced arthritis in rats, thus providing preclinical pharmacodynamic information for subsequent clinical studies.

1. Experimental Method:

1. Adjuvant Preparation:

100 mg *Mycobacterium tuberculosis* H37Ra was weighed, grinded for about 5 minutes, washed the mortar 3 times with paraffin oil, the final concentration was 10 mg/ml. The *Mycobacterium tuberculosis* H37Ra was broken in ultrasound and ultrasonic treated in ice-water mixture for about 30 min.

2. Inducing Arthritis:

① The adjuvant was shaken and mixed well, and extracted with a 1 mL glass syringe (20 G needle), and a 25 G needle was replaced. Before immunizing each rat, it was necessary to rotate the syringe constantly to avoid the precipitation of *Mycobacterium tuberculosis*.

② The rat was put into an anesthesia machine for anesthesia (isoflurane), and immunized after anesthesia. The site was the left foot of the rat, and subcutaneously injected with 0.1 ml.

③ The normal group (5 animals) was injected with 0.1 ml paraffin oil, and the immunized part was subcutaneously in the left foot of the rat.

The first time for adjuvant injection was day 0.

3. Administration and Dosage Design 3.1 On the 13rd day, all animals showed symptoms of arthritis such as erythema or redness on the feet, and were grouped according to the experimental protocol according to body weight and score. Two standards of each group was basically consistent, the grouping situation was shown in Table 1. 76 Rats were divided into 5 groups, 10 in each group and the normal group have 5 animals.

3.2 According to Table 1, the dosage of each group was as shown in Table 3 below. Twice a day for a total of 14 days.

TABLE 3

Grouping and dosage design

| Group | Test drug | Number | Route of administration | Dose mg/kg | Frequency of administration |
|---|---|---|---|---|---|
| G1 | Normal | 5 | N/A | N/A | N/A |
| G2 | control (vehicle group) | 10 | p.o. | N/A | Bid, 14 d |
| G3 | Dexamethasone (Dex.) | 10 | p.o. | 0.3 | Qd, 14 d |
| G6 | Compound 4-3 | 10 | p.o. | 15 | Bid, 14 d |
| G7 | Compound 8-2 | 10 | p.o. | 5 | Bid, 14 d |
| G8 | Compound 8-2 | 10 | p.o. | 15 | Bid, 14 d |

4. Determination of the Incidence of Arthritis

Weight: Weigh three times a week from the 13rd day to the 27th day.

Foot volume: measured once before immunization, and measured three times a week from the 13rd day to the 27th day.

Scoring: From the 13rd day to the 27th day, the scoring was three times a week. Depending on the different degrees of lesions (redness, joint deformation), according to a scoring of 0-4 points, the maximum score of each limb was 4 points, and the maximum score for each animal was 12 points (except for the injection of left hind limb). The scoring criteria was shown in Table 4.

TABLE 4

Clinical scoring criteria for arthritis

| Score | Clinical symptoms |
|---|---|
| 0 | No erythema and swelling |
| 1 | Erythema or slight swelling near metatarsal or ankle or metatarsal, or a toe with erythema and swelling |
| 2 | Slight erythema and swelling of ankle and metatarsal, two or more than two toes with erythema and swelling |
| 3 | Moderate erythema and swelling of ankle, wrist and metatarsal |
| 4 | Severe swelling of ankle, wrist, metatarsal and toe |

5. Statistical Processing

The experimental data was expressed by mean standard error (Mean SEM), and the area under the foot volume curve (AUC) was analyzed by one-way ANOVA, $p<0.05$ was considered to be significant difference.

2. Experimental Results:

1. Weight

Compared with the normal group, the weight of rat decreased after immunization modeling, and the weight of the rat in each administration group decreased from the 15th day to the 17th day, and then the weight began to recover slowly. Among them, the vehicle control group had the largest weight loss; the dose groups subjected to compound 8-2 began to recover slowly on the 19th day, as shown in FIG. 1.

Figure 2:
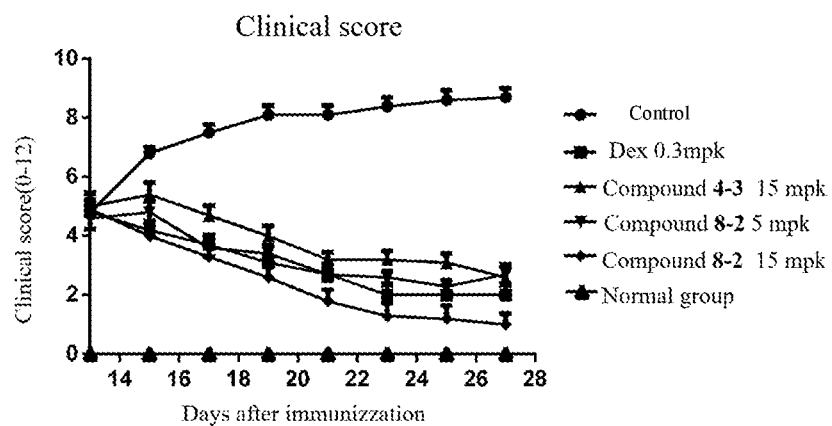
FIG. 2: Clinical score of arthritis.

2. Clinical Scoring:

On the 6th day after adjuvant immunization, symptoms of arthritis appeared in rats. The experimental results were shown in FIG. 2. The average clinical score of the vehicle control group reached about 8.5 as a peak on the 24th day, marking the successful establishment of the AIA model (FIG. 2). At the end of the experiment (the 27th day), compound 4-3 (15 mpk) and compound 8-2 (5 mpk and 15 mpk) significantly inhibited the clinical scores of arthritis rats (compared to the vehicle control group, p values were <0.0001, <0.0001 and <0.0001 respectively), and the clinical scores of arthritis rats were reduced to 2.6, 2.7, and 1.0, respectively (the p value was 0.0004 compared the high dose group with the low dose group). At the same time, Dexamethasone (dexamethasone, Dex.) 0.3 mg/kg treatment can significantly inhibit the clinical score of collagen-induced arthritis. From the 23rd day, the clinical score was maintained at about 2.0 until the end of the experiment.

3. Foot Volume and Area Under the Curve AUC

Figure 3:
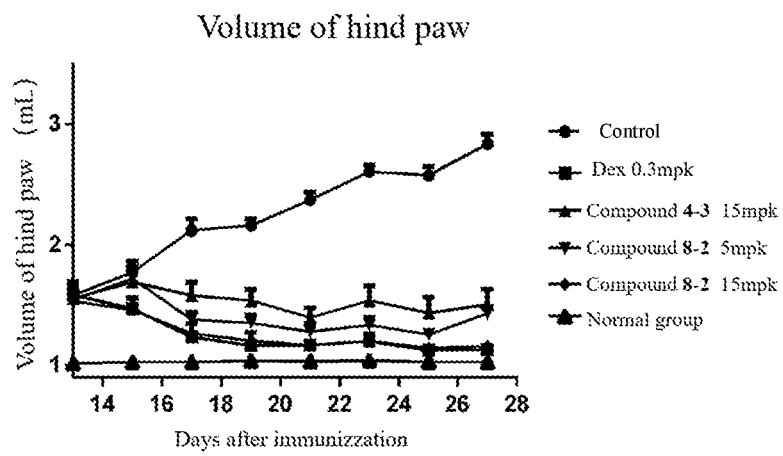
FIG. 3: Change curve of foot volume.

Similar to the clinical score results, the experimental results were shown in FIG. 3: The average foot volume of the vehicle control animals increased steadily from 1.6 mL on the 3rd day to 2.8 mL at the end of the experiment on the 27th day, marking the successful establishment of the AIA model (FIG. 3). At the end of the experiment, all doses can significantly inhibit the increase in the foot volume of arthritis rats (compared with the vehicle control group, p value was <0.0001), and the average foot volume of arthritis rat was reduced to 1.5 mL, 1.4 mL and 1.1 mL respectively, wherein compound 8-2 was dose-dependent (p<0.0001 compared the high dose group with the low dose group). Dexamethasone 0.3 mg/kg well suppressed the increase of the average foot volume. After administration, the foot volume of this group decreased steadily to the end of the experiment, which was maintained at 1.1 mL.

Figure 4:
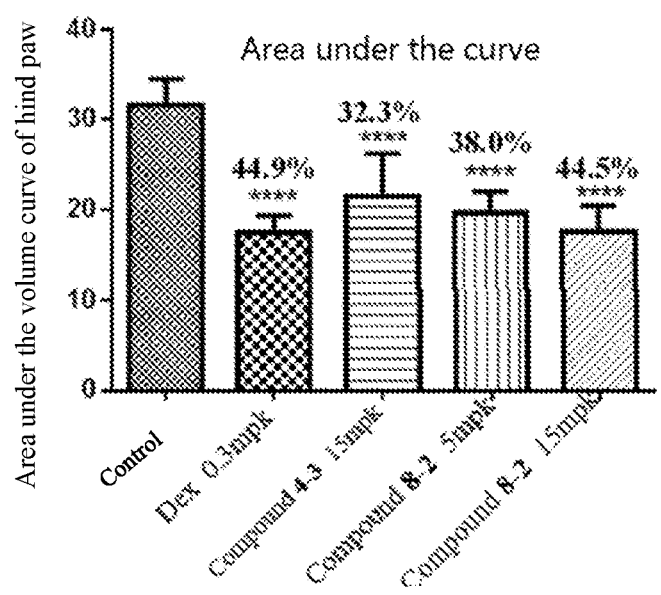
FIG. 4: Inhibition rate of each administration group relative to the vehicle control group.

By analyzing the foot volume curve of each animal in each group, the area under the curve AUC was calculated, and the inhibition rate of each administration group relative to the vehicle control group was calculated by the average AUC between groups. The results were shown in FIG. 4. Compound 4-3 (15 mg/kg) and compound 8-2 (5 mg/kg and 15 mg/kg) had an inhibition rate of 32.3%, 38.0% and 44.5% in the administration group. Compared with the vehicle control group, the AUC of each group was significantly different (p values were 0.0011, <0.0001 and <0.0001, respectively), and they were dose-dependent (compared the AUC of the high dose group with that of the low dose group, p value was <0.01). Dexamethasone inhibition rate was 44.9%. (FIG. 4).

Conclusion: Compound 4-3 (15 mpk) and compound 8-2 (5 mpk, 15 mpk) significantly inhibited the clinical scores of arthritis rats at various doses, the foot volume decreased steadily after the administration, body weight gradually recovered, AUC calculated by the area under the foot volume curve was significantly higher than that of vehicle control group.

What is claimed is:

1. A compound of formula (I), a tautomer or a pharmaceutically acceptable salt thereof,

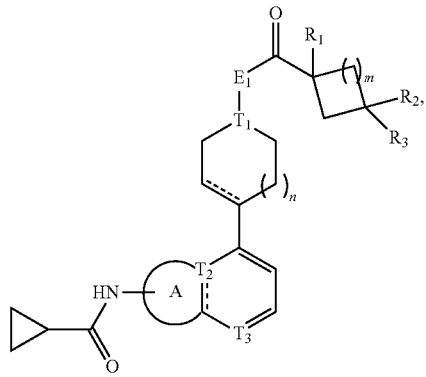
(I)

wherein, is a single bond or a double bond;
m is 0 or 1;
n is 0 or 1;
$E_1$ is a single bond, —CH$_2$— or —NH—;
$T_1$ is CH or N;
$T_2$ is C or N;
$T_3$ is CH or N;
ring A is 1,2,4-triazolyl or thiazolyl;
$R_1$ is H, F, Cl, Br, I, OH, NH$_2$, CN or a C$_{1-3}$ alkyl, wherein the C$_{1-3}$ alkyl is optionally substituted by one, two or three $R_a$;
each of $R_2$ and $R_3$ is independently H, F, Cl, Br, I, OH, NH$_2$ or CN;
$R_a$ is F, Cl, Br, I, OH or NH$_2$.

2. The compound, the tautomer or the pharmaceutically acceptable salt thereof as defined in claim 1, wherein, $R_1$ is H, F, Cl, Br, I, OH, NH$_2$, CN or Me.

3. The compound, the tautomer or the pharmaceutically acceptable salt thereof as defined in claim 1, $R_2$ is H, F, Cl, Br, I, OH, NH$_2$ or CN.

4. The compound, the tautomer or the pharmaceutically acceptable salt thereof as defined in claim 1, $R_3$ is H, F, Cl, Br, I, or OH.

5. The compound, the tautomer or the pharmaceutically acceptable salt thereof as defined in claim 1, wherein the structural unit

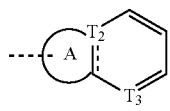

is

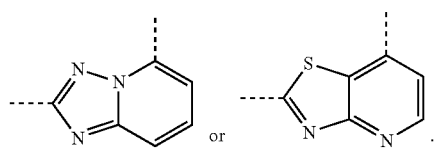

6. The compound, the tautomer or the pharmaceutically acceptable salt thereof as defined in claim 1, wherein the structural unit

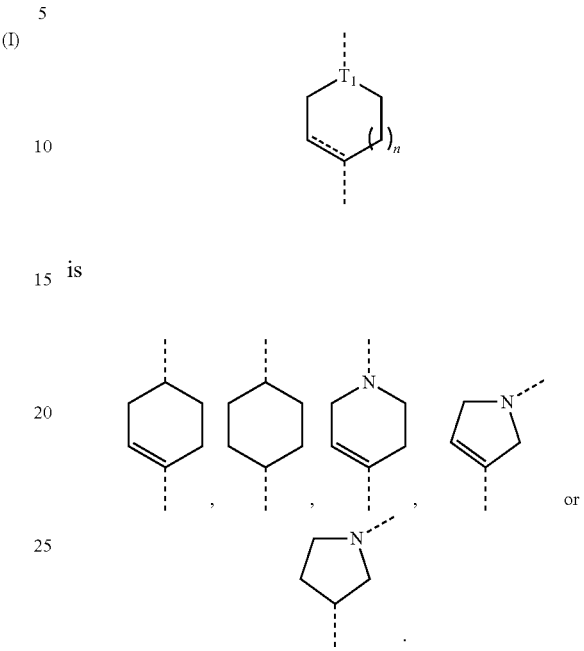

is

7. The compound, the tautomer or the pharmaceutically acceptable salt thereof as defined in claim 1, wherein the compound is a compound of formula (I-1), (I-2), (I-3), (I-4) or (I-5),

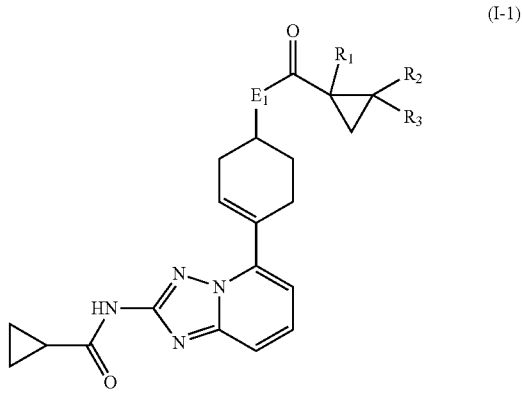
(I-1)

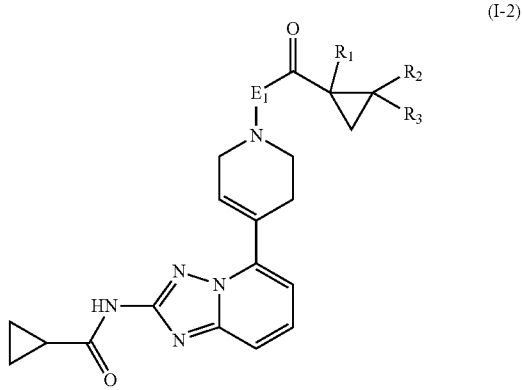
(I-2)

-continued
(I-3)
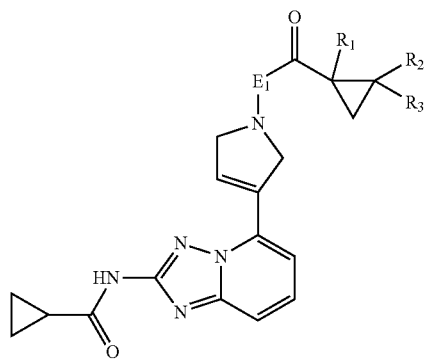
(I-4)
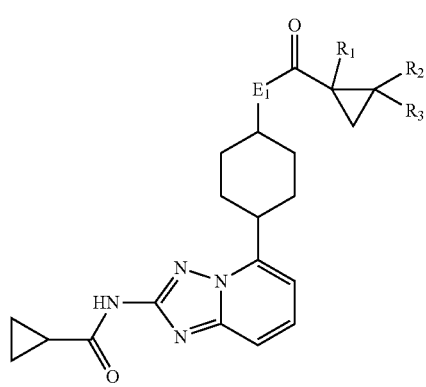
(I-5)
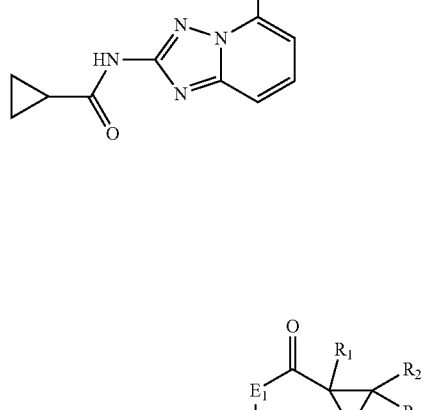
wherein,
E₁ is as defined in claim 1;
R₁ is as defined in claim 1;
R₂ is as defined in claim 1;
R₃ is as defined in claim 1.
8. A compound, a tautomer or a pharmaceutically acceptable salt thereof, wherein the compound is selected from the group consisting of
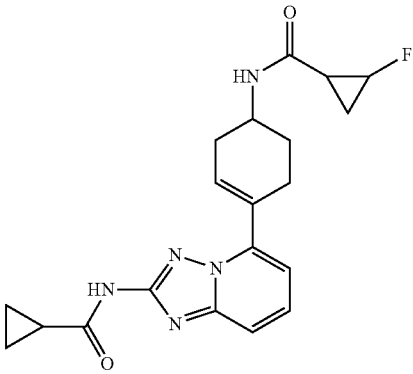
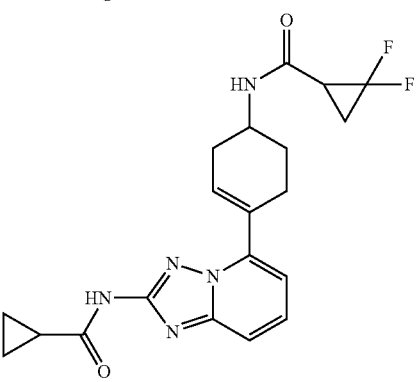
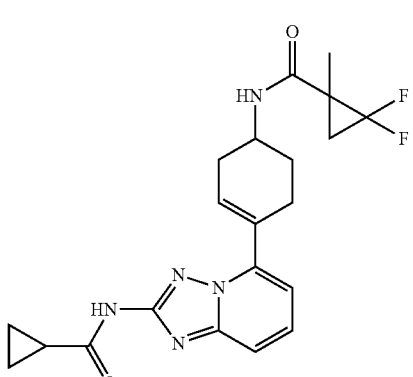
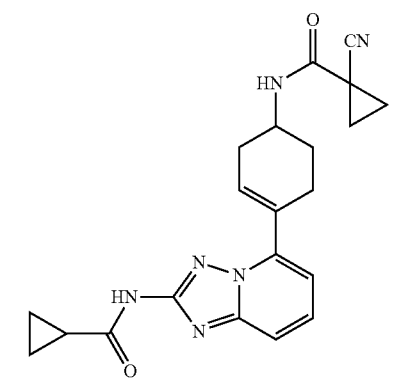

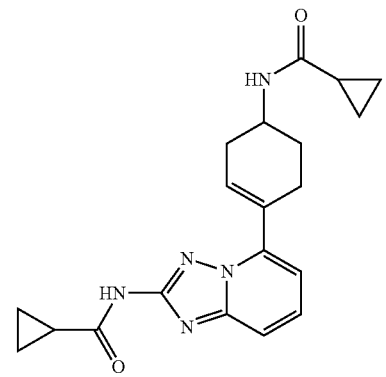
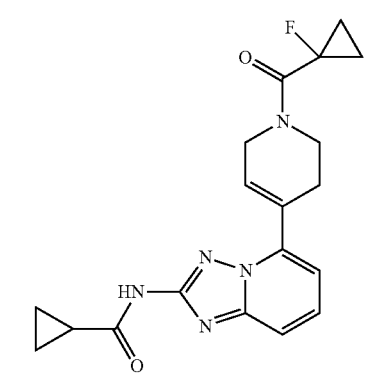
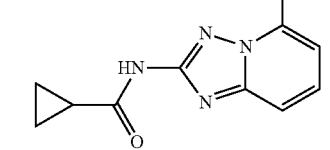
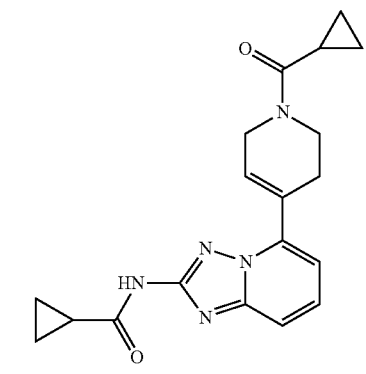
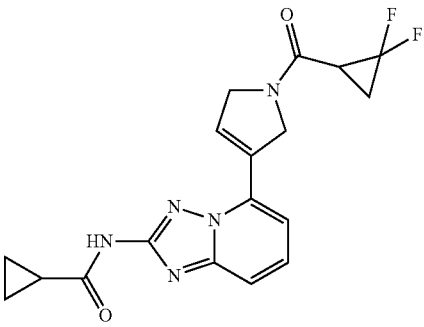
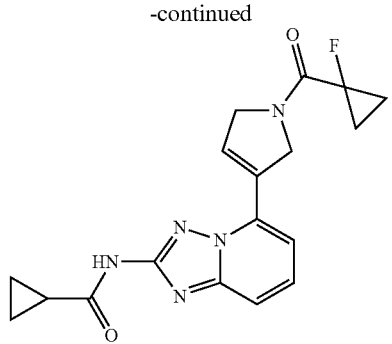
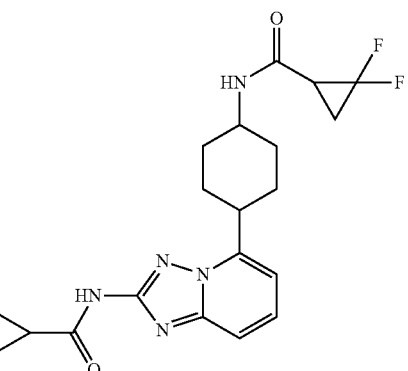
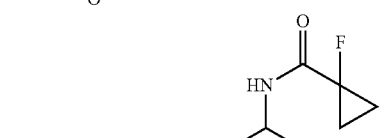
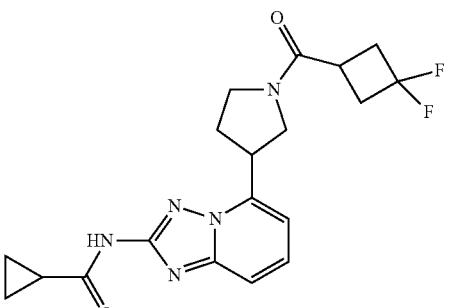
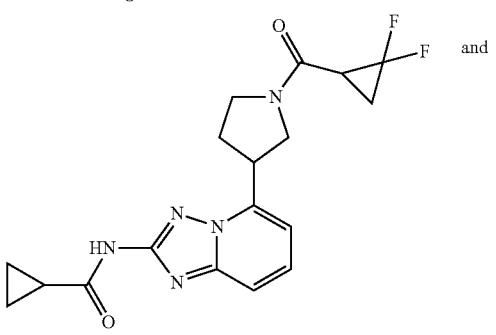
and

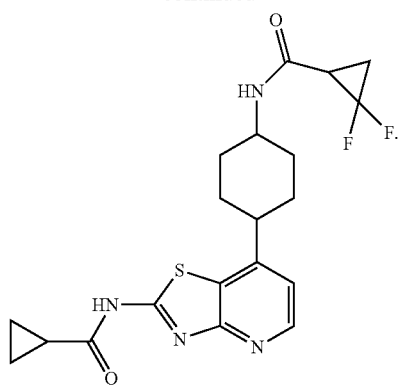
9. The compound, the tautomer or the pharmaceutically acceptable salt thereof as defined in claim 8, wherein the compound is selected from the group consisting of
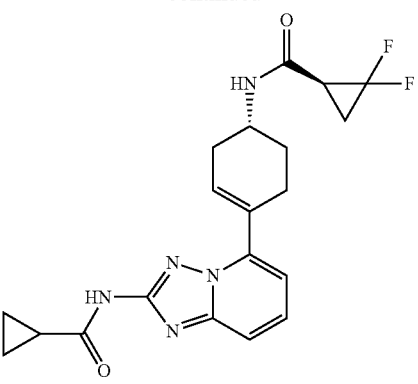
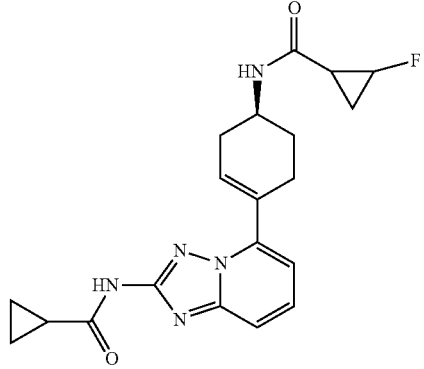
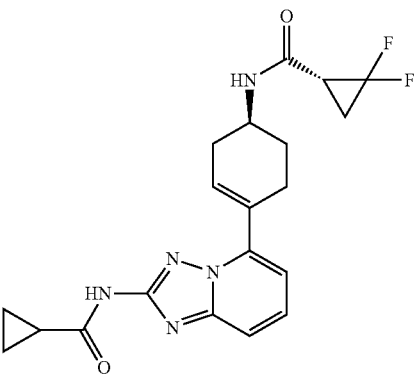
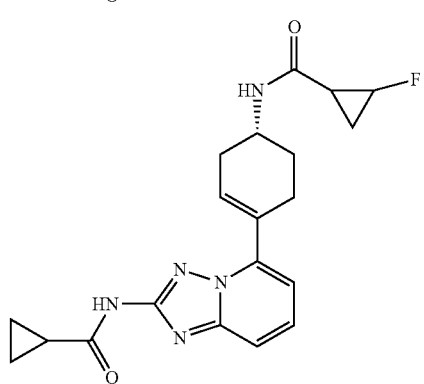
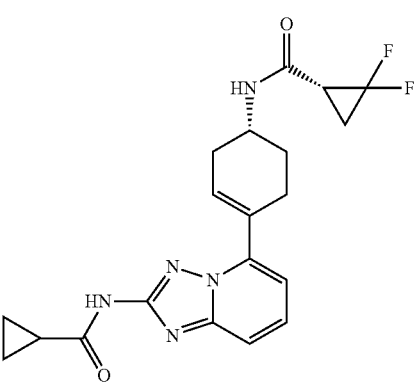
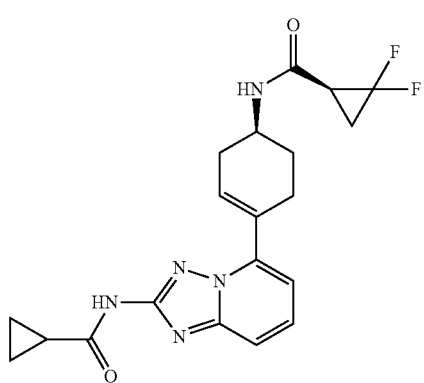
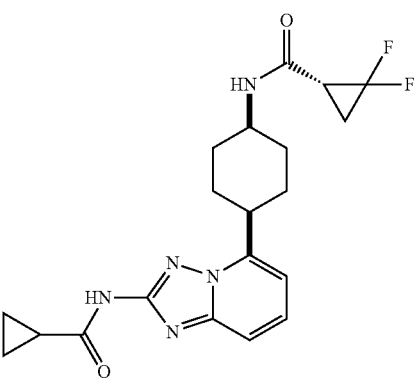

-continued

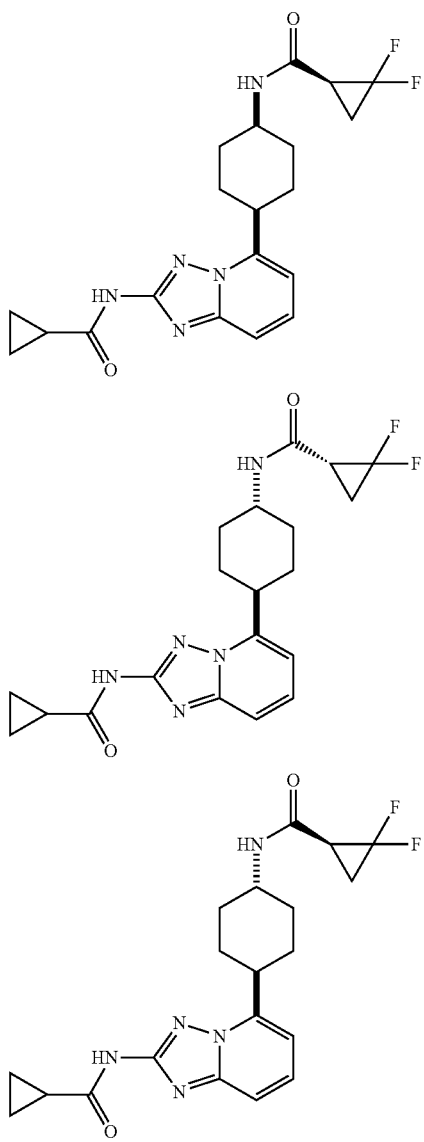

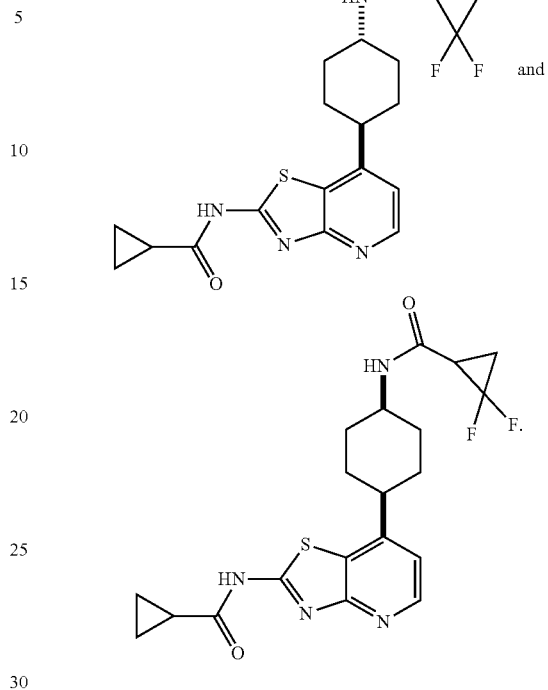

10. A pharmaceutical composition, which comprises a therapeutically effective amount of the compound, the tautomer or the pharmaceutically acceptable salt thereof as defined in claim 1 as an active ingredient, and a pharmaceutically acceptable carrier.

11. A method for treating JAK1 and TYK2 related disease in a subject in need thereof, comprising administrating the compound, the tautomer or the pharmaceutically acceptable salt as defined in claim 1 to the subject, wherein the JAK1 and TYK2 related disease is rheumatoid arthritis.

12. A method for treating JAK1 and TYK2 related diseases in a subject in need thereof, comprising administrating the pharmaceutical composition as defined in claim 10 to the subject, wherein the JAK1 and TYK2 related disease is rheumatoid arthritis.

\* \* \* \* \*